(12) United States Patent
Bartfeld et al.

(10) Patent No.: US 9,468,925 B2
(45) Date of Patent: Oct. 18, 2016

(54) TISSUE CONTAINER FOR MOLECULAR AND HISTOLOGY DIAGNOSTICS INCORPORATING A BREAKABLE MEMBRANE

(71) Applicant: Becton, Dickinson and Company, Franklin Lakes, NJ (US)

(72) Inventors: Benjamin R. Bartfeld, Ringwood, NJ (US); C. Mark Newby, Tuxedo, NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 14/296,779

(22) Filed: Jun. 5, 2014

(65) Prior Publication Data
US 2014/0286837 A1   Sep. 25, 2014

Related U.S. Application Data

(62) Division of application No. 13/167,114, filed on Jun. 23, 2011, now Pat. No. 8,802,034, which is a division of application No. 12/257,134, filed on Oct. 23, 2008.

(60) Provisional application No. 60/982,057, filed on Oct. 23, 2007.

(51) Int. Cl.
*A61B 10/00* (2006.01)
*A61J 1/06* (2006.01)
(Continued)

(52) U.S. Cl.
CPC ............ *B01L 3/502* (2013.01); *A61B 10/0096* (2013.01); *G01N 1/28* (2013.01); *B01L 2300/042* (2013.01); *B01L 2300/0672* (2013.01); *G01N 1/31* (2013.01)

(58) Field of Classification Search
CPC ............ G01N 1/31; G01N 1/28; G01N 1/30; G01N 1/36; G01N 2001/315; B01L 2300/042; B01L 2300/0672; B01L 2300/0609; B01L 2300/02; B01L 2300/044; B01L 2300/046; B01L 2300/0858; B01L 2200/026; B01L 2300/041; B01L 3/508; A61B 10/0096; A61B 5/150496; B65D 41/28; B65D 51/002
USPC ......... 422/50, 401, 405, 408, 413, 417, 534, 422/536, 554, 560, 561, 562, 565, 566; 435/36, 325
See application file for complete search history.

(56) References Cited

U.S. PATENT DOCUMENTS

| 4,034,884 A | 7/1977 | White |
|---|---|---|
| 4,076,592 A | 2/1978 | Bradley |

(Continued)

FOREIGN PATENT DOCUMENTS

| DE | 20201894 U1 | 5/2002 |
|---|---|---|
| EP | 0018380 A1 | 11/1980 |

(Continued)

*Primary Examiner* — Dean Kwak
(74) *Attorney, Agent, or Firm* — The Webb Law Firm

(57) ABSTRACT

A container for storing a biological sample for molecular diagnostic testing and/or histological testing is provided. The container includes a first chamber for receiving a sample holder therein, a second chamber, and a closure for enclosing the container. A breakable membrane, such as a piercable foil, extends within the container and separates the two chambers. When the breakable membrane is broken, fluid can pass between the first and second chambers. The membrane may be broken through an activator on the closure, such as a depressible member or a rotatable carrier, causing the sample holder to break through the membrane.

6 Claims, 18 Drawing Sheets

(51) Int. Cl.
*B01L 3/00* (2006.01)
*G01N 1/28* (2006.01)
*G01N 1/31* (2006.01)

(56) References Cited

U.S. PATENT DOCUMENTS

| | | | |
|---|---|---|---|
| 4,220,252 | A | 9/1980 | Beall et al. |
| 4,416,984 | A | 11/1983 | Wheeler, Jr. |
| 4,903,869 | A | 2/1990 | McKenna |
| 5,393,496 | A * | 2/1995 | Seymour ............... 422/413 |
| 5,424,040 | A | 6/1995 | Bjornsson |
| 5,658,531 | A | 8/1997 | Cope et al. |
| 6,207,408 | B1 | 3/2001 | Essenfeld et al. |
| 6,375,028 | B1 * | 4/2002 | Smith ............... 220/258.1 |
| 6,899,850 | B2 * | 5/2005 | Haywood et al. ......... 422/547 |
| 7,147,826 | B2 | 12/2006 | Haywood et al. |
| 7,837,939 | B2 * | 11/2010 | Tung ............ A61B 10/0045 422/410 |
| 2002/0048819 | A1 | 4/2002 | Alley |
| 2003/0021727 | A1 * | 1/2003 | Weyker et al. ............ 422/58 |
| 2003/0086830 | A1 | 5/2003 | Haywood et al. |
| 2003/0129738 | A1 | 7/2003 | Sorenson et al. |
| 2004/0038269 | A1 | 2/2004 | Birnboim |
| 2004/0052682 | A1 * | 3/2004 | Yokoi et al. ............ 422/58 |
| 2004/0184954 | A1 | 9/2004 | Guo et al. |
| 2005/0163660 | A1 | 7/2005 | Wang |
| 2006/0245977 | A1 | 11/2006 | Bodner |
| 2007/0215496 | A1 | 9/2007 | Scarborough |
| 2007/0275475 | A1 * | 11/2007 | Liang ............... 436/165 |
| 2008/0025877 | A1 | 1/2008 | Alley |
| 2009/0024060 | A1 * | 1/2009 | Darrigrand et al. ....... 600/584 |
| 2009/0100944 | A1 | 4/2009 | Newby |
| 2009/0104699 | A1 | 4/2009 | Newby et al. |
| 2009/0105611 | A1 | 4/2009 | Wilkinson et al. |
| 2009/0183581 | A1 | 7/2009 | Wilkinson et al. |
| 2010/0255484 | A1 * | 10/2010 | Halverson et al. ............ 435/6 |

FOREIGN PATENT DOCUMENTS

| | | |
|---|---|---|
| EP | 0332753 A1 | 9/1989 |
| GB | 1234044 A | 6/1971 |
| JP | 4965889 | 6/1974 |
| JP | 59113886 A | 6/1984 |
| JP | 10281953 A | 10/1988 |
| JP | 4140635 A | 5/1992 |
| JP | 06078746 A | 3/1994 |
| JP | 2000510703 A | 8/2000 |
| JP | 2001194365 A | 7/2001 |
| JP | 2003057232 A | 2/2003 |
| JP | 2011502254 A | 1/2011 |
| WO | 7901131 A1 | 12/1979 |
| WO | 03031065 A1 | 4/2003 |
| WO | 03044488 A1 | 5/2003 |
| WO | 2006041297 A2 | 4/2006 |
| WO | 2007016935 A1 | 2/2007 |
| WO | 2008040812 A1 | 4/2008 |

* cited by examiner

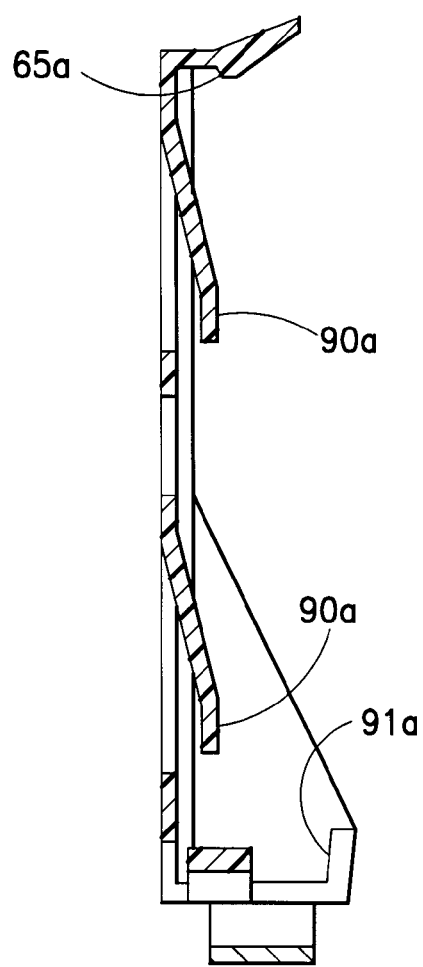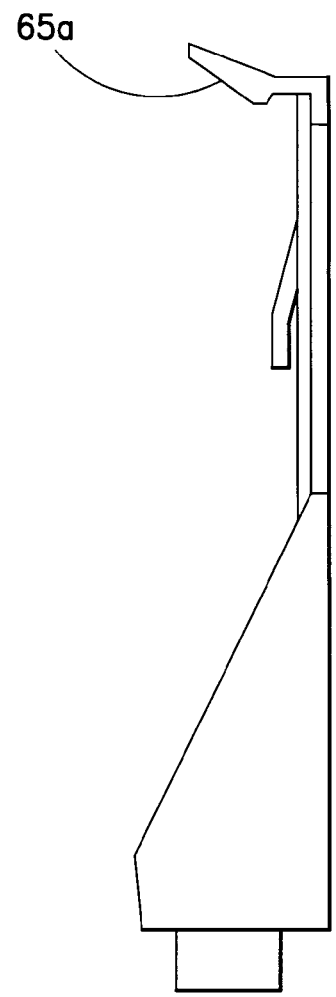
FIG.14C            FIG.14D
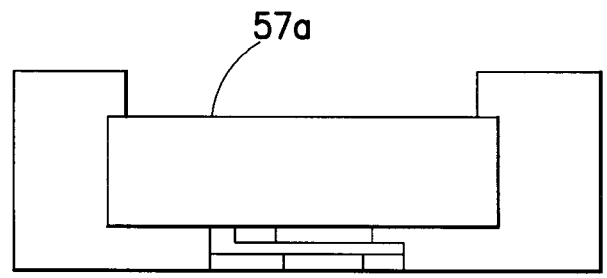
FIG.14E

TISSUE CONTAINER FOR MOLECULAR AND HISTOLOGY DIAGNOSTICS INCORPORATING A BREAKABLE MEMBRANE

CROSS REFERENCE TO RELATED APPLICATION

This application is divisional application of U.S. patent application Ser. No. 13/167,114 filed Jun. 23, 2011, which is a divisional application of U.S. patent application Ser. No. 12/257,134, filed Oct. 23, 2008, entitled "Tissue Container for Molecular and Histology Diagnostics Incorporating a Breakable Membrane", which claims priority to U.S. Provisional Patent Application No. 60/982,057, filed Oct. 23, 2007, entitled "Tissue Container For Molecular and Histology Diagnostics Incorporating a Breakable Membrane", the entire disclosures of each of which are herein incorporated by reference.

BACKGROUND OF THE INVENTION

1. Field of the Invention

The present invention relates to a tissue sample container. More particularly, the present invention relates to a sample container for containing a biological tissue specimen for molecular diagnostic testing and/or histological testing.

2. Description of Related Art

Biological samples are often obtained by a researcher or clinician for diagnostic evaluation to determine the presence of certain diseases and to determine an appropriate treatment for the disease. Tissue samples are often obtained from a patient for molecular diagnostic and nucleic acid analysis, particularly RNA and DNA analysis, which have become common place in research for the treatment of numerous diseases. An essential requirement for accurate RNA and DNA analysis is the presence of high quality and intact RNA and DNA within the biological sample.

Oftentimes, the histologic or cytologic analysis will be performed immediately after the sample is removed from the patient or source to avoid molecular changes that may occur during storage. These changes, such as gene transcription, result from the degradation of the nucleic acids within the sample caused by exposure of an untreated sample to certain environmental stresses. However, analysis of the sample immediately after the sample is collected is often impossible or impractical. Therefore, it is necessary to provide a system for storing a sample under controlled conditions for a certain period of time while maintaining the structural and molecular integrity of the sample.

Traditionally, one way of accomplishing this storage is by submerging the sample in a single fixative reagent. A typical fixative reagent is ten percent (10%) formalin but may also include water, miscible alcohols, ethanol/acetone mixtures, and ethanol/acetic acid mixtures. The containers used for such storage are generally composed of a single integral cavity which could house an effective volume of reagent to treat a particular biological tissue sample. The biological tissue sample is placed in the container along with the reagent, the container is closed, and the sample is then stored and transported while being preserved by the fixative agent. An example of such a container can be seen in U.S. Pat. No. 7,147,826 to Haywood et al. Such containers have experienced some success in the industry, but are subject to certain limitations.

SUMMARY OF THE INVENTION

In accordance with an embodiment of the present invention, a container for storing a biological sample includes a housing extending between a first open end and a second end defining a container interior. The container includes a removable closure for enclosing the first open end, and at least one breakable membrane separating the container interior into at least a first chamber and a second chamber. The second chamber is in fluid isolation from the first chamber, with the first chamber aligned with the first open end of the housing and adapted to receive a sample holder therein. The breakable membrane is breakable to establish fluid communication between the first chamber and the second chamber.

The sample holder may be detachably connected to the closure for insertion into the first chamber of the container interior. The closure may be threadably matable with the housing. In one configuration, the sample holder may be rotatable with respect to the closure to maintain the sample holder in a substantially stationary position within the first chamber during engagement of the closure with the housing. Optionally, the container may include a platform attached to the closure and adapted for receiving the sample holder for insertion into the first chamber of the container interior. In a further configuration, the closure may be threadably matable with the housing, and the platform may be rotatable with respect to the closure to maintain the sample holder in a stationary position within the first chamber during engagement of the closure with the housing.

The sample holder may include a closable housing defining an internal cavity for holding a biological sample, with the housing having a plurality of fluid openings adapted for allowing fluid contained within at least one of the first chamber and the second chamber to pass into the internal cavity. In one configuration, the sample holder is a histology cassette. Optionally, a first fluid may be disposed within the first chamber and a second fluid may be disposed within the second chamber with the first fluid being different than the second fluid.

At least one breakable membrane may be a pierceable foil. In a further configuration, the housing may have a longitudinal axis and the breakable membrane may extend across at least a portion of the container interior transverse to the longitudinal axis, thereby establishing the first and second chambers. Alternatively, the housing may have a longitudinal axis, and the breakable membrane may extend across at least a portion of the container interior parallel to the longitudinal axis, thereby establishing the first and second chambers. The container may further include a second breakable membrane spaced apart from the breakable membrane and extending across at least a portion of the container interior parallel to the longitudinal axis with the first chamber being established between the breakable membrane and the second breakable membrane.

The container may also include a movable structure extending from the container interior to an exterior of the container such that movement of the movable structure causes the breakable membrane to break, thereby establishing fluid communication between the first and second chambers. The moveable structure may include a depressible element and the sample holder may be connected to the depressible element such that depressing the depressible element causes at least a portion of the sample holder to break the breakable membrane. The depressible element may be a flexible elastomeric button. A removable cover may be disposed over the depressible element to prevent movement of the depressible element. Alternatively, the moveable structure may include a rotatable carrier and the sample holder may be connected to the rotatable carrier such that rotation of the rotatable carrier causes at least a portion of the sample holder to break the breakable membrane.

In accordance with another embodiment of the present invention, a container for storing a biological sample includes a housing having a first open end, a second end, and defining a container interior. The housing has a longitudinal axis. The container also includes a breakable membrane extending across the container interior transverse to the longitudinal axis separating the container interior into at least a first chamber and a second chamber. The breakable membrane is breakable to establish fluid communication between the first chamber and the second chamber. The first chamber is aligned with the first open end of the housing and is adapted to receive a sample holder therein. The container also includes a removable closure for enclosing the first open end. The removable closure includes a depressible element with the sample holder connected therewith, such that depressing the depressible element causes at least a portion of the sample holder to break the breakable membrane.

In accordance with another embodiment of the present invention, a container for storing a biological sample includes a housing having a first open end, a second end, and a sidewall extending therebetween defining a container interior. The housing has a longitudinal axis. The container also includes a first breakable membrane extending across the container interior parallel to the longitudinal axis, and a second breakable membrane spaced apart from the first breakable membrane and extending across the container interior parallel to the longitudinal axis. A first chamber is established between the first breakable membrane and the second breakable membrane, and a second chamber is established between the housing wall and at least one of the first breakable membrane and the second breakable membrane. The first chamber is aligned with the first open end of the housing and is adapted to receive a sample holder therein. At least one of the first breakable membrane and the second breakable membrane is breakable so as to establish fluid communication between the first and second chambers. The container further includes a removable closure for enclosing the first open end. The removable closure includes a rotatable carrier and having the sample holder connected therewith, wherein rotation of the rotatable carrier causes at least a portion of the sample holder to break at least one of the first and second the breakable membranes.

In accordance with yet another embodiment of the present invention, a method of storing a biological sample within at least one liquid includes the step of providing a container having a housing extending between a first open end and a second end and defining a container interior. The container includes at least one breakable membrane separating the container interior into at least a first chamber and a second chamber. The first chamber is aligned with the first open end of the housing and is adapted to receive a sample holder therein. At least the second chamber contains a liquid therein and is isolated from the first chamber by the breakable membrane. The method further includes the step of inserting a sample holder containing a biological sample into the first chamber of the container housing. The method also includes the step of breaking the breakable membrane to establish fluid communication between the first chamber and the second chamber, such that the liquid contained within the second chamber contacts the biological sample within the first chamber.

Optionally, the container includes a removable closure for covering the first open end of the housing, with the sample holder movably connected with the closure. The step of breaking the breakable membrane further includes moving at least a portion of the sample holder with respect to the closure to break the breakable membrane.

BRIEF DESCRIPTION OF THE DRAWINGS

FIG. 14C is a side sectional view of the platform taken along line A-A of FIG. 14B.

FIG. 14D is a side view of the platform of FIG. 14A.

FIG. 14E is a top view of the platform of FIG. 14A.

DESCRIPTION OF PREFERRED EMBODIMENTS

Figure 1:
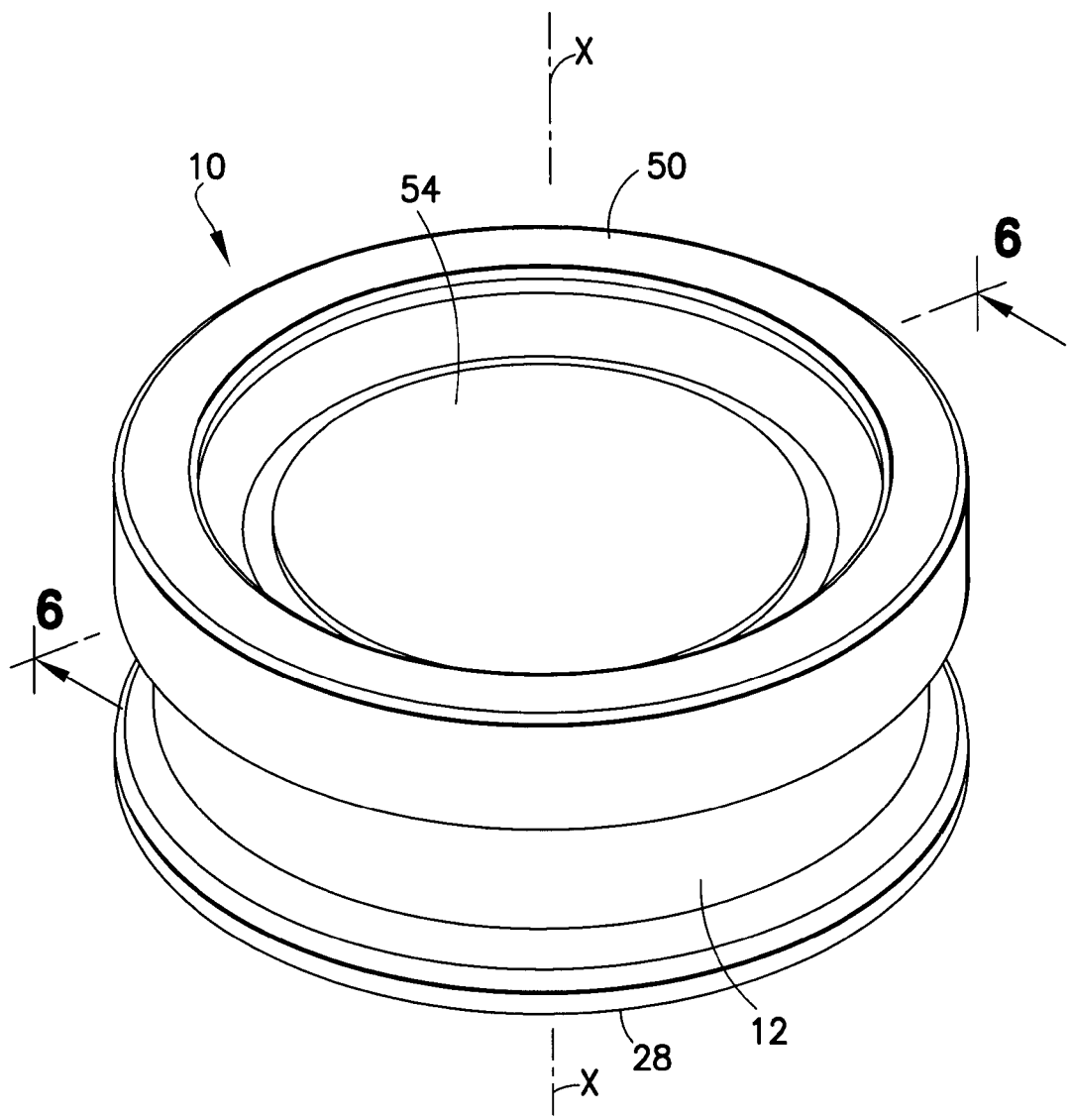
FIG. 1 is a perspective view of a container for storing a biological sample in accordance with an embodiment of the present invention.
Figure 2:
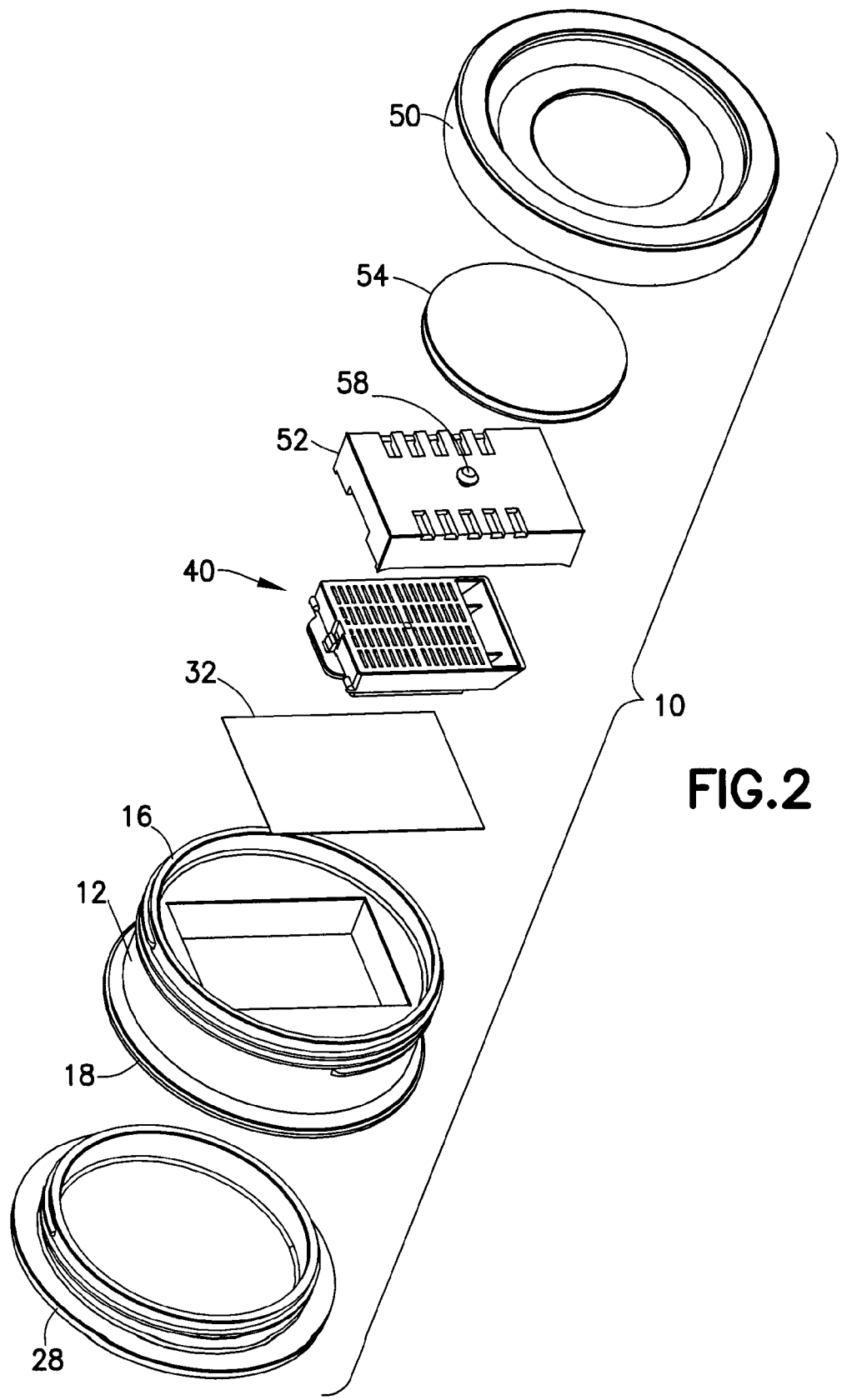
FIG. 2 is an exploded perspective view of the container of FIG. 1.

For purposes of the description hereinafter, spatial orientation terms, if used, shall relate to the referenced embodiment as it is oriented in the accompanying drawing figures or otherwise described in the following detailed description. However, it is to be understood that the embodiments described hereinafter may assume many alternative variations and embodiments. It is also to be understood that the specific devices illustrated in the accompanying drawing figures and described herein are simply exemplary and should not be considered as limiting.

The container of the present invention allows for storage of a biological sample, such as a tissue sample for molecular and histology diagnostics, and in particular histopathology testing. In particular, the container includes an open end and a closed end, with a breakable membrane separating the container interior into a first chamber and a second chamber in fluid isolation from each other. Accordingly, a liquid medium may be contained in at least one of the chambers, such as the second chamber. In this manner, a tissue sample contained in, for example, the first chamber may be handled or processed prior to contacting the tissue with the solution in the second chamber. As will be discussed in greater detail herein, in one embodiment of the invention, the first chamber may be empty representing a storage chamber, and the second chamber may include a liquid medium, such as a reagent in the form of a tissue fixative solution for fixing a sample for histopathology diagnostics. In this manner, a tissue sample may be placed within the first chamber, and when desired, the membrane separating the first and second chambers may be broken so as to place the tissue sample in fluid contact with the solution within the second chamber.

In a further embodiment of the invention, the first chamber may contain a first fluid, such as a tissue fixative solution, and the second chamber may contain a second fluid, such as a reagent in the form of a nucleic acid stabilization solution, such that a tissue sample may be placed in the first chamber in fluid contact with the first fluid for a desired time period, after which the membrane separating the first chamber from the second chamber may be broken so as to also place the tissue sample in fluid contact with the solution within the second chamber. The embodiments described herein are representative of containers capable of use in any of these manners.

Referring to the drawings, in which like reference characters refer to the like parts throughout the several views thereof, FIGS. 1-6 illustrate a container 10 in accordance with an embodiment of the present invention. Generally, container 10 includes a housing 12, a first chamber 20, a second chamber 26, a breakable membrane 32, a closure 50, and a sample holder 40. The individual components of container 10 may be made of any suitable material that is impervious to liquid and/or gas, such as glass and/or plastic. In one embodiment, the housing 12 may be made of one or more than one of the following representative materials: polypropylene, polyethylene terephthalate (PET), glass, or combinations thereof.

Container 10 generally includes a housing 12 having a housing wall 14 extending between a first open end 16 and a second end 18, defining an axis X of the container, designated for purposes herein as a central or longitudinal axis, along with a container interior. As will be discussed in more detail herein, a breakable membrane 32 extends transversely across the axis of the interior of housing 12 separating housing 12 into a first chamber 20 and a second chamber 26.

In particular, housing wall 14 defines first chamber 20, with first open end 16 extending into the first chamber 20. First chamber 20 defines a first intended fill volume and may include a cavity that may be sized so as to receive and accommodate sample holder 40 therein, as will be discussed in more detail. For example, first chamber 20 may include a bottom wall surface defined by breakable membrane 32. Breakable membrane 32 may extend entirely across the interior of housing 12, thereby extending about the entire interior perimeter or surface of housing wall 14. Alternatively, a wall surface 22 may extend radially inwardly from portions of the interior of housing wall 14 across the interior of housing 12, with downwardly extending side wall surfaces 24a, 24b, 24c, and 24d and the bottom wall surface defined by breakable membrane 32 defining a generally rectangular shaped cavity generally corresponding to the size and shape of sample holder 40.

Housing wall 14 further defines second chamber 26 below breakable membrane 32, defining a second intended fill volume, which is desirably different than the first intended fill volume of the first chamber 20. Second chamber 26 may be positioned adjacent the bottom or second end 18 of housing 12. Second end 18 may be an open end extending into second chamber 26. In such an arrangement, container 10 further includes a cover 28 for mating with housing 12 over the second end 18, thereby providing a closable access to second chamber 26. Cover 28 may be matable with housing 12 in any manner, such as a frictional fit, snap fit, threadable engagement, interlocking structural engagement, or other manner, providing a liquid tight seal. For example, corresponding threads may be provided about the perimeter of an external surface of cover 28 and within the perimeter of an internal surface of housing wall 14 of housing 12 at second end 18, or may be provided within the perimeter of an internal surface of cover 28 and about the perimeter of an external surface of housing wall 14 of housing 12 at second end 18.

Figure 6A:
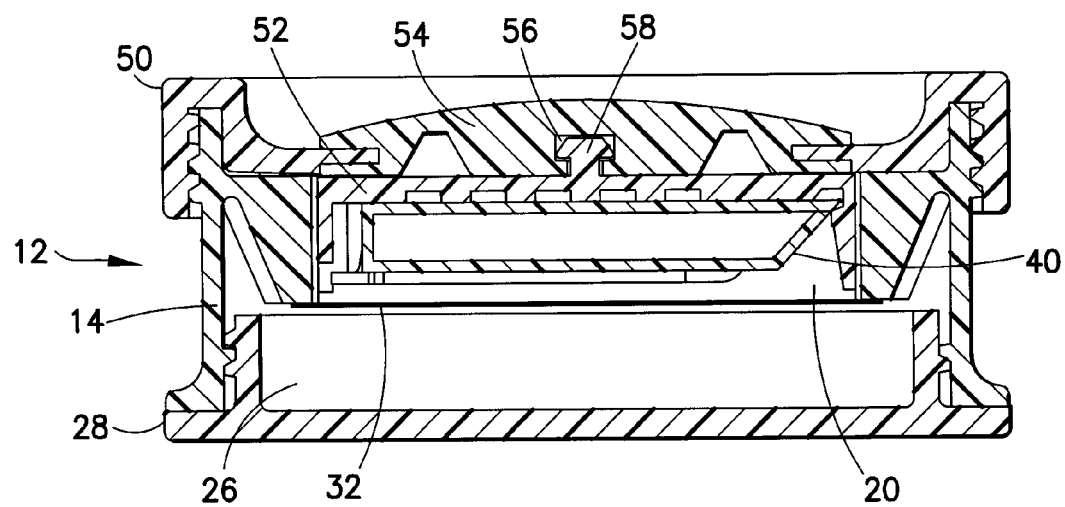
FIG. 6A is a cross-sectional view of the container taken along lines 6-6 of FIG. 1 with the sample holder contained within the first chamber.
Figure 6B:
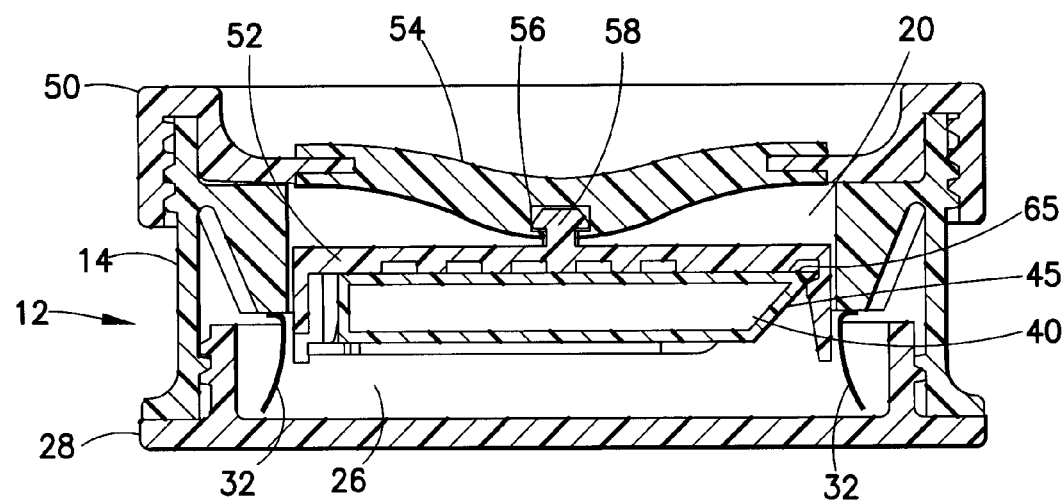
FIG. 6B is a cross-sectional view of the container as shown in FIG. 6A after the breakable membrane has been broken.
Figure 6C:
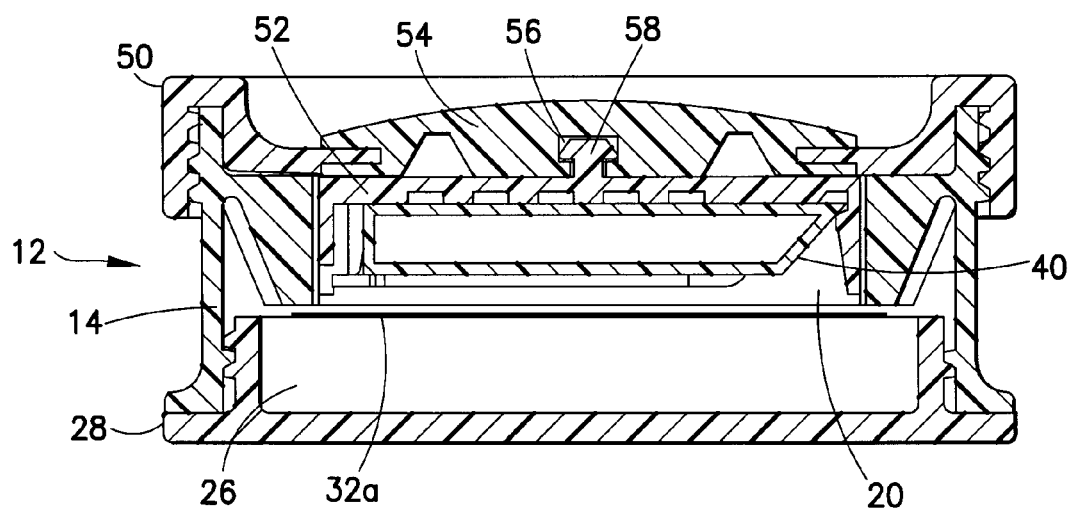
FIG. 6C is a cross-sectional view of a container shown in an alternate embodiment with the breakable membrane extending across cover 28.
Figure 7:
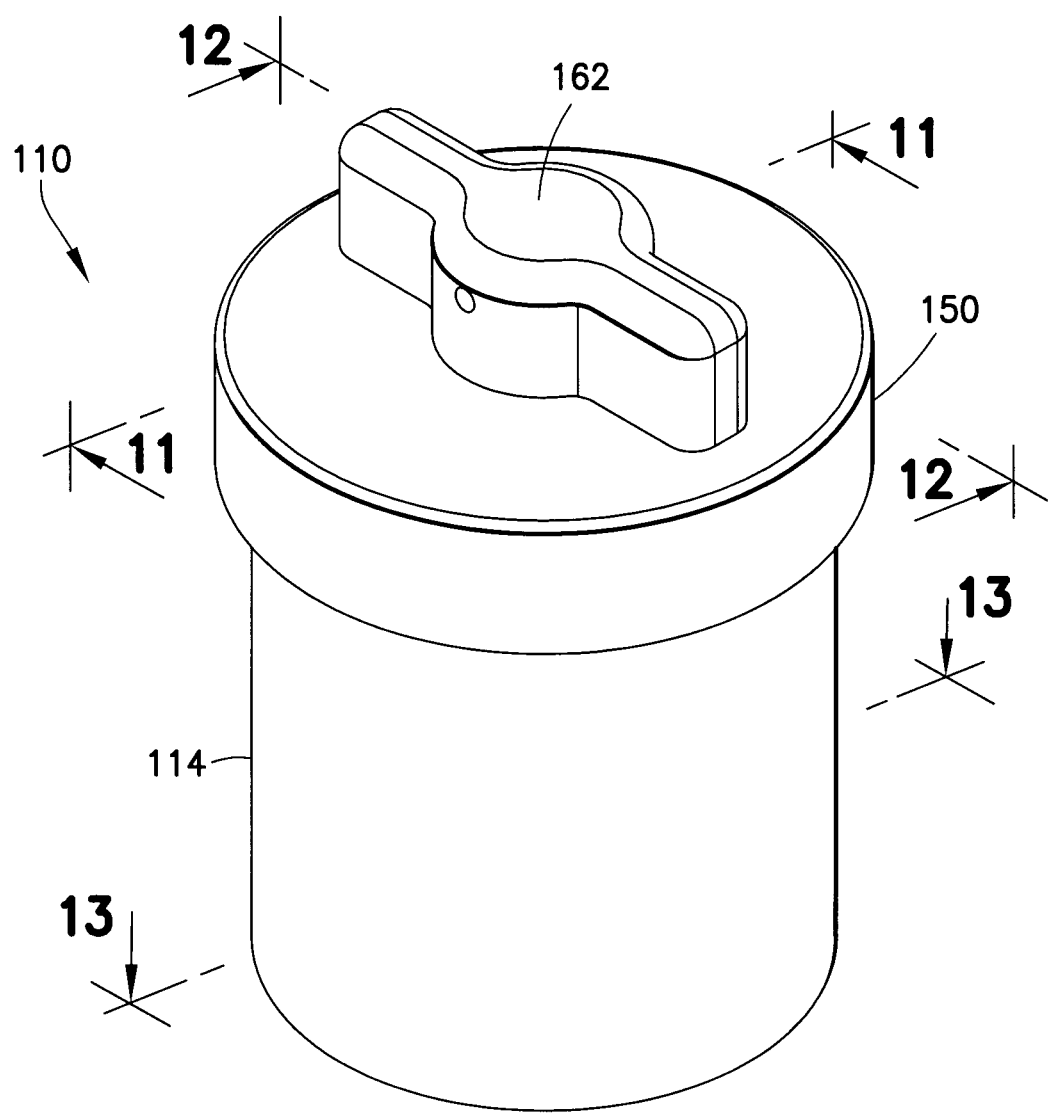
FIG. 7 is a perspective view of a container system for storing a biological sample in accordance with a further embodiment of the present invention.
Figure 8:
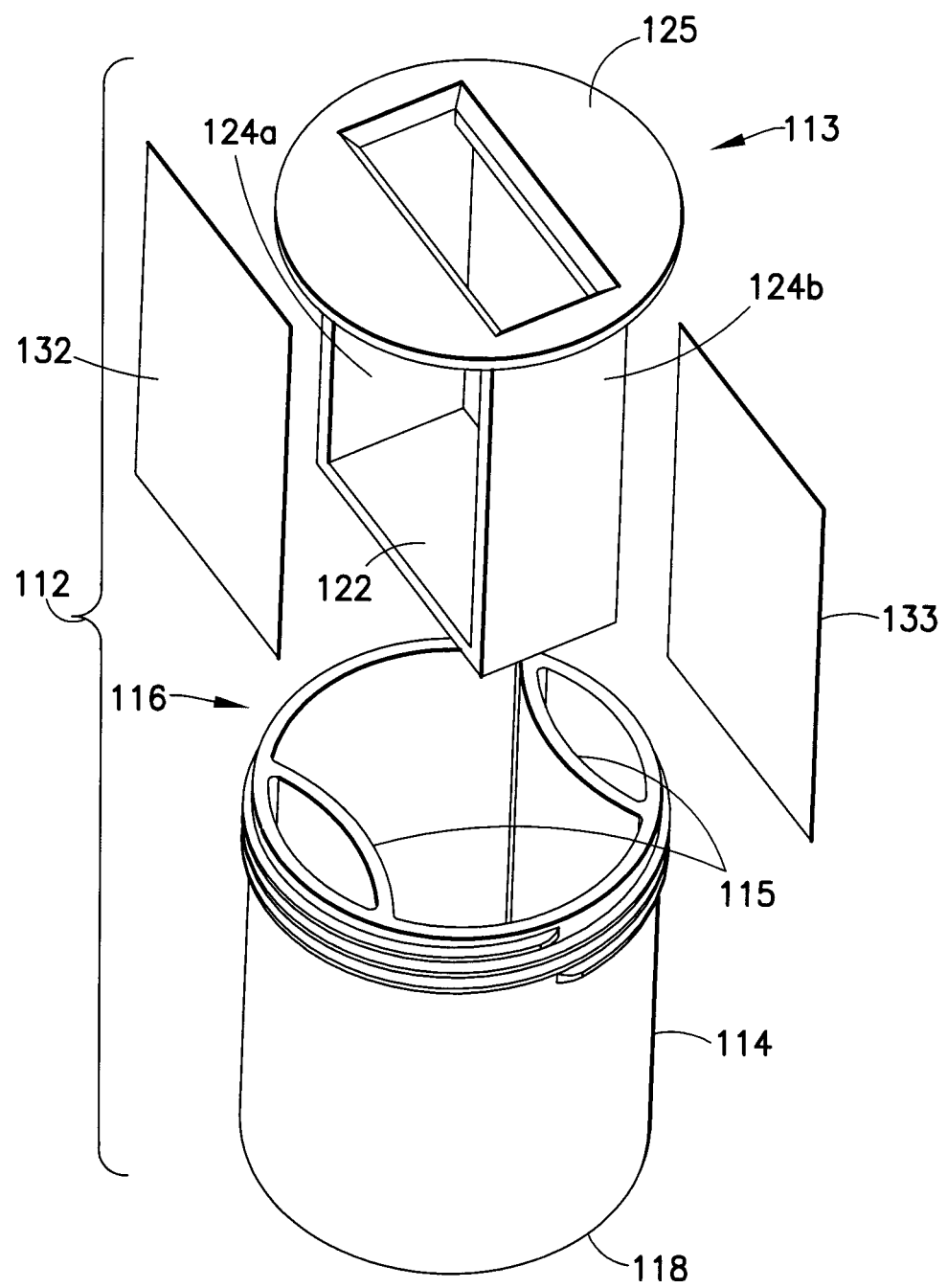
FIG. 8 is an exploded perspective view of the housing of the container of FIG. 8.
Figure 9:
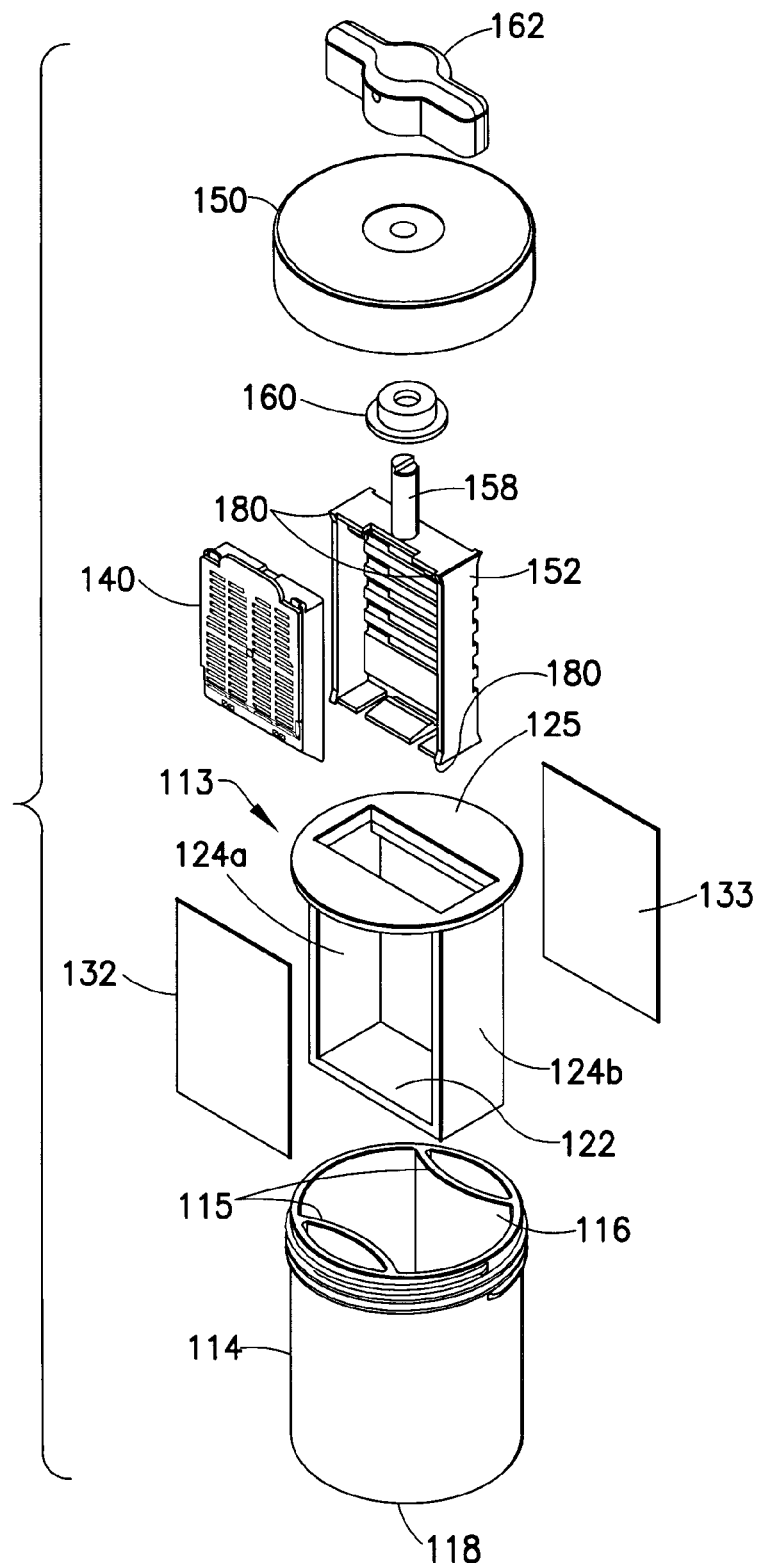
FIG. 9 is an exploded perspective view of the container of FIG. 7.

In an alternative embodiment shown in FIG. 6C, breakable membrane 32a may extend across cover 28 as opposed to extending between surfaces 24a, 24b, 24c, and 24d. In this manner, second chamber 26 is formed below breakable membrane 32a as a separate structure with cover 28, which can be matable with housing 12 as described above.

Sample holder 40 is further provided for use with container 10 and is adapted to be received within first chamber 20 of housing 12. Sample holder 40 may form a part of container 10 or may be separately provided for use with container 10. Sample holder 40 may be in the form of a conventional histology cassette (a "histo-cassette") as is known in the art for storing a biological tissue sample during preparation of the sample for diagnostic testing. Such sample holders or histo-cassettes are known for containing biological specimens during processing with fluids to prepare the specimen for later analyses. Typically, such sample holders or histo-cassettes are generally rectangular, planar housing structures having an internal cavity, with a plurality of openings through the wall surface to provide fluid flow through the housing. Often, a removable or openable cover encloses the structure, such as through a hinge situated along one end of the housing structure for providing a door-like cover to the housing structure. Also, a planar surface, which may be slanted, is often provided in such sample holders or histo-cassettes acting as a surface for labeling or writing. The dimensions for such a sample holder, for example, may include a height of about 0.3 inch (plus or minus 0.1 inch), a length of about 1.73 inches (plus or minus 0.1 inch), and a width of about 1.12 inches (plus or minus 0.1 inch). Examples of sample holders that may be useful herein are shown in U.S. Pat. No. 4,220,252 to Beall et al. and U.S. Pat. No. 4,034,884 to White, both of which are expressly incorporated herein by reference.

Figure 3A:
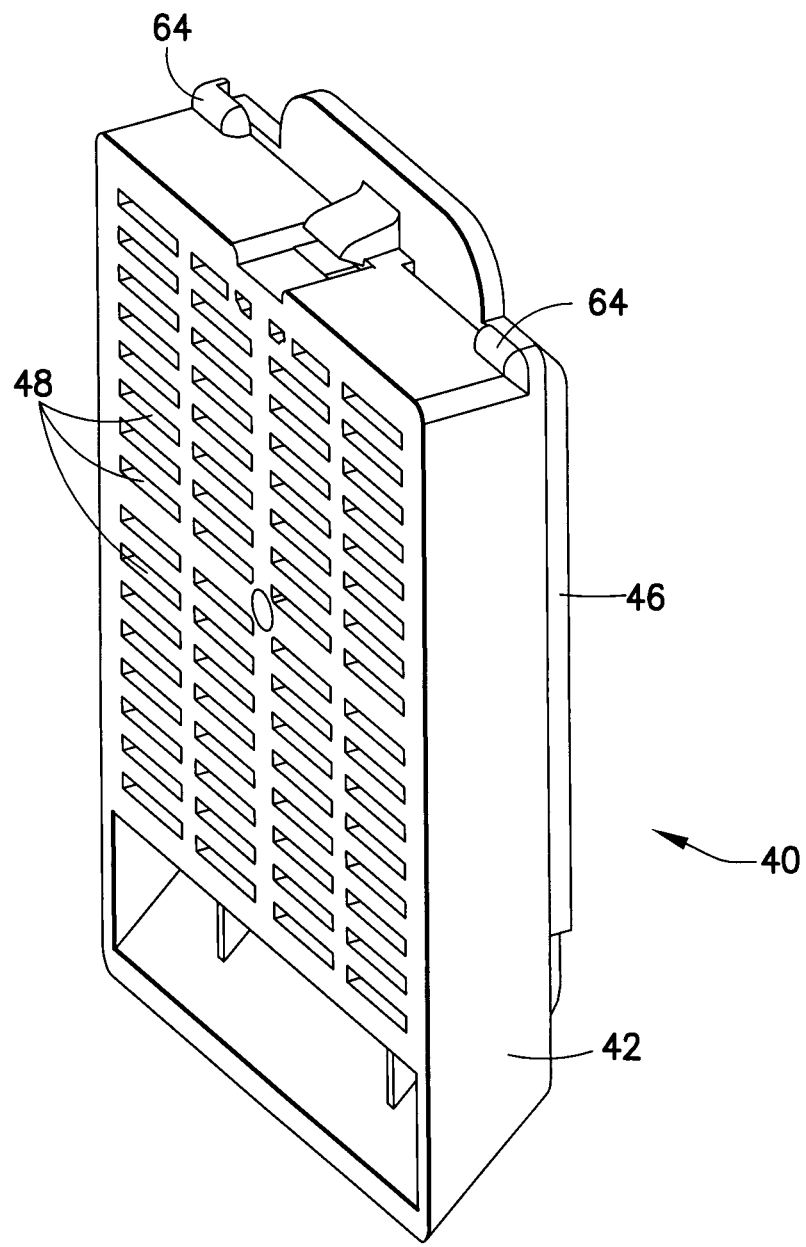
FIG. 3A is a perspective view of a sample holder of the container of FIG. 1 in an embodiment of the present invention.
Figure 3B:
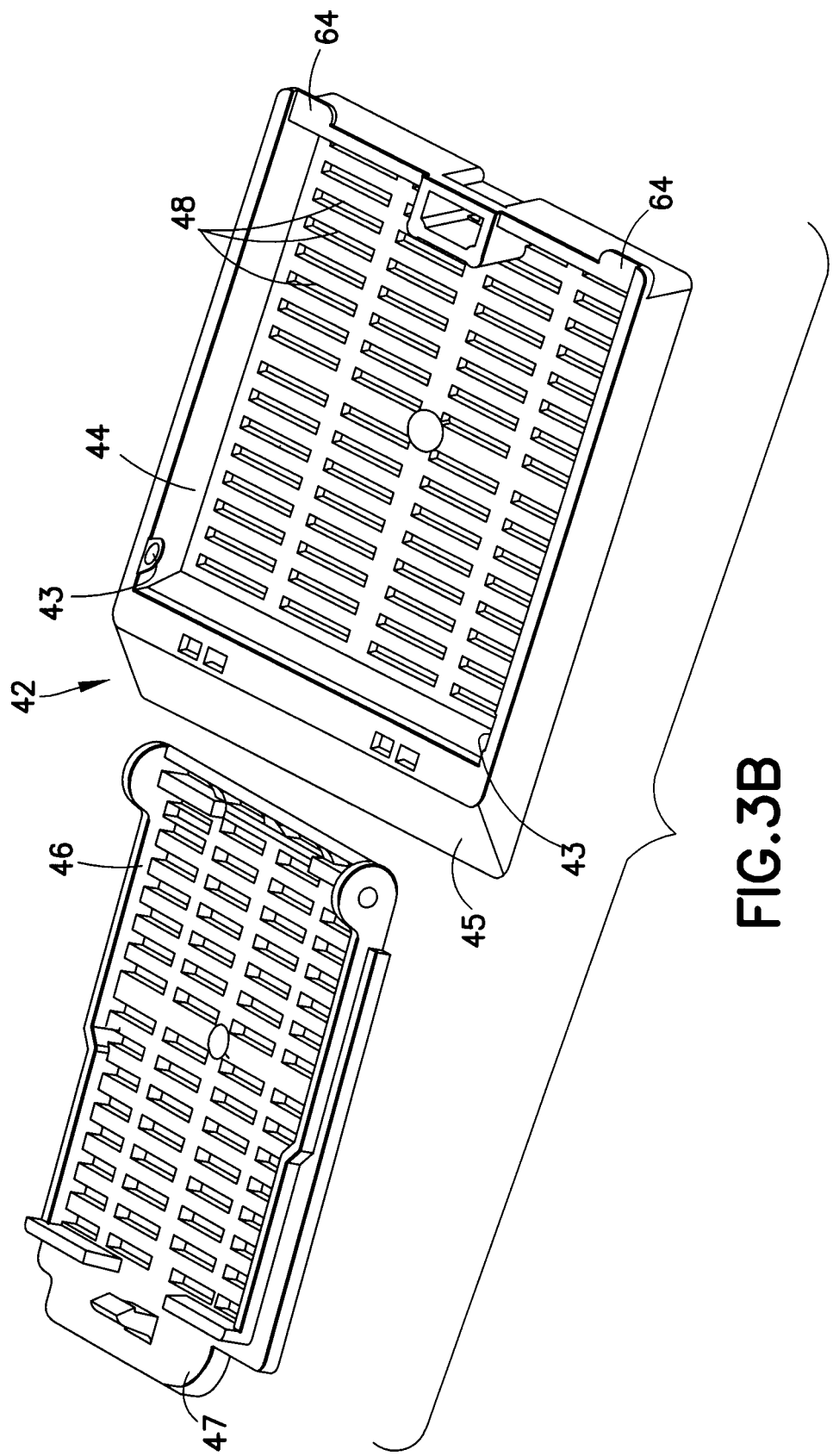
FIG. 3B is a perspective view of the sample holder of FIG. 3A shown in an open position.

For example, as shown in FIGS. 3A and 3B, sample holder 40 includes a generally rectangular planar housing 42 having opposing walls defining an internal cavity 44 for holding a biological tissue sample therein. At least one of the walls of housing 42 may be slanted, such as slanted wall 45, providing a surface for applying a label or for writing, so as to provide a mechanism for identification of a sample contained within sample holder 40, as appropriate. Housing 42 of sample holder 40 is a closable structure, and may include a hinged door-like structure 46 attached with housing 42 thereby permitting access to the internal cavity 44 for storing a tissue sample within or removing a tissue sample from internal cavity 44. The door-like structure 46 may be integrally formed with housing 42 so as to provide a unitary structure with the door 46 connected to housing 42 through a flap to provide a mechanism for pivoting door 46 with respect to housing 42, or door 46 may be otherwise connectable to housing 42, such as through a pivot point 43 acting as a hinge for opening door 46 from one side of housing 42 to gain access to the internal cavity 44. Housing 42 of sample holder 40 includes at least one, and preferably a plurality of, fluid openings 48 adapted to allow fluid to flow therethrough. In this manner, when housing 42 is positioned within first chamber 20, fluid within first chamber 20 can flow through openings 48 and contact the biological tissue sample contained within internal cavity 44.

Container 10 further includes closure 50 for enclosing the first open end 16 of housing 12. Closure 50 is matable with housing 12 at first open end 16 in any manner, such as a frictional fit, snap fit, threadable engagement, interlocking structural engagement, or other manner providing a liquid tight seal. Desirably, closure 50 and housing 12 include corresponding threads such that closure 50 can be threaded with housing 12 to provide a liquid tight seal therebetween. For example, such corresponding threads may be provided about the perimeter of an external surface of closure 50 and within the perimeter of an internal surface of housing wall 14 of housing 12 at first end 16 or may be provided within the perimeter of an internal surface of closure 50 and about the perimeter of an external surface of housing wall 14 of housing 12 at first end 16.

Figure 4A:
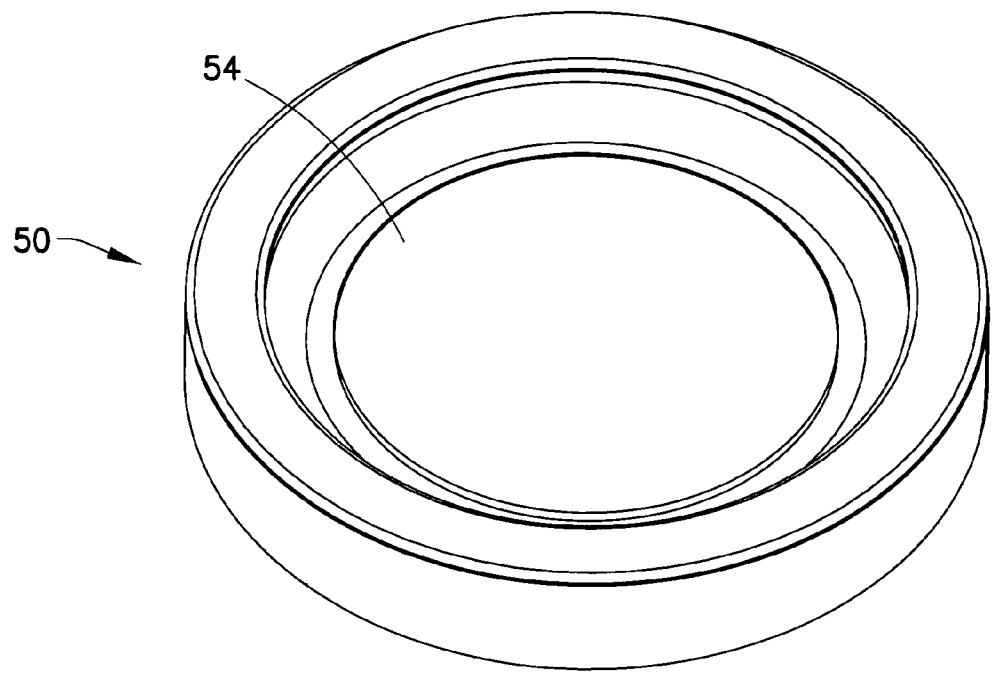
FIG. 4A is a top perspective view of a closure of the container of FIG. 1 in an embodiment of the present invention.
Figure 4B:
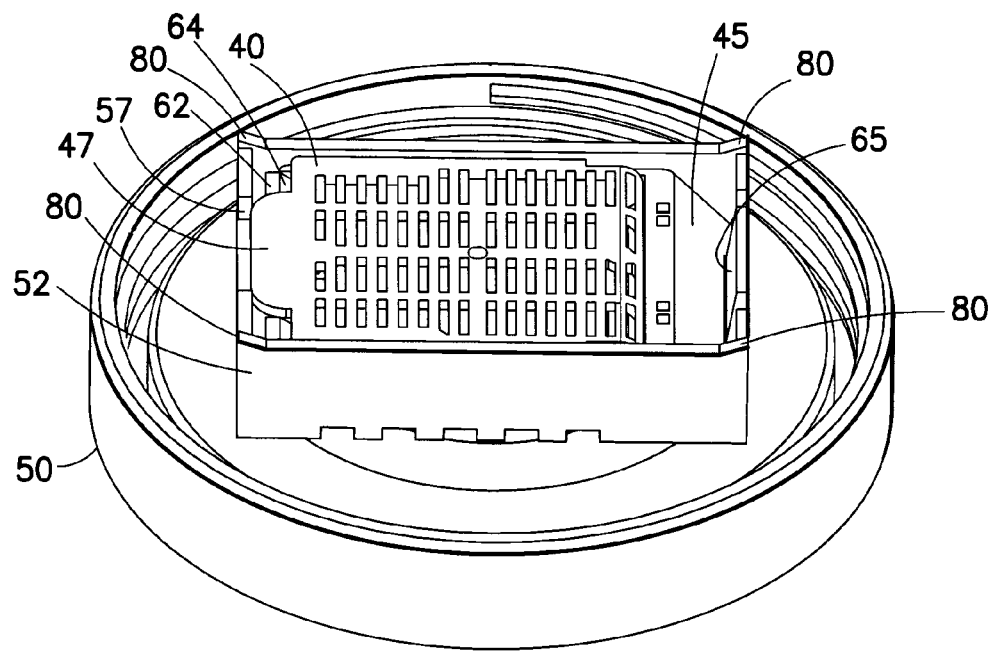
FIG. 4B is a bottom perspective view of the closure of FIG. 4A including a sample holder therewith.
Figure 4C:
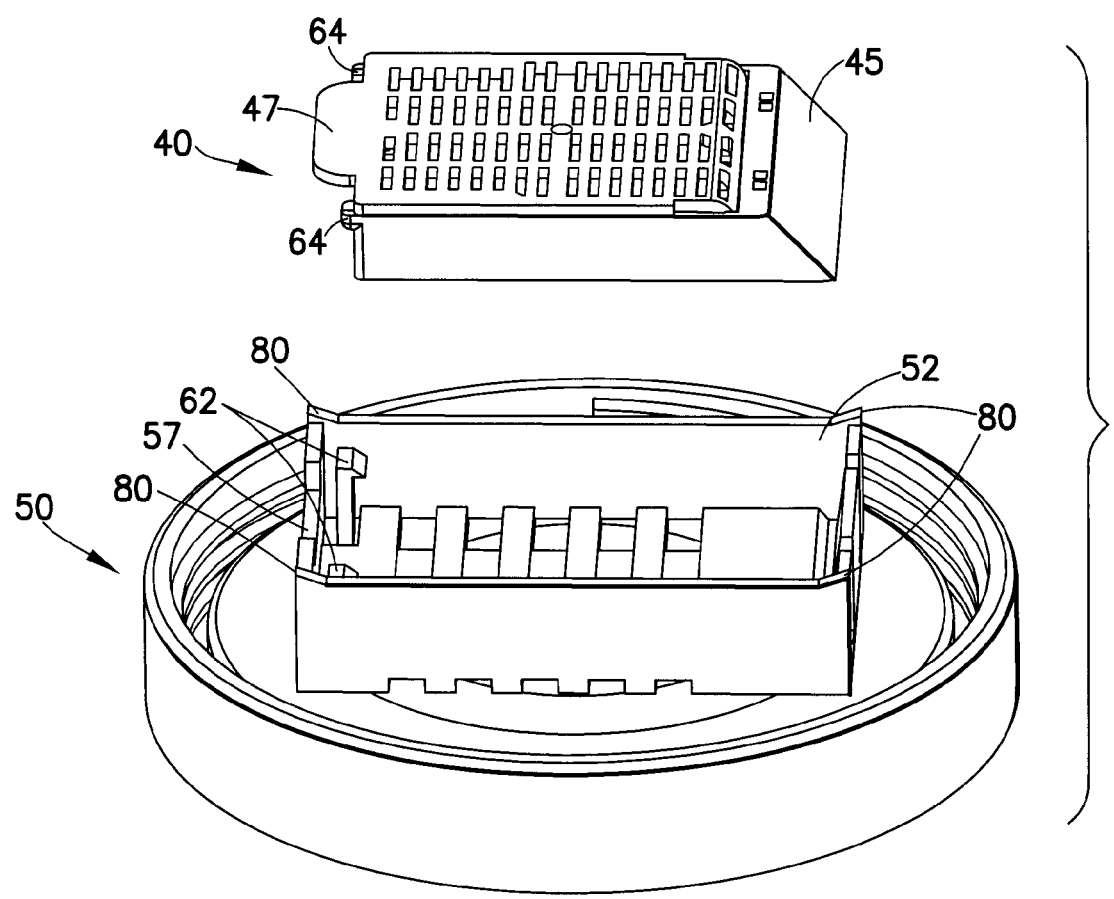
FIG. 4C is a bottom perspective view of the closure of FIG. 4A including a sample holder shown separately.
Figure 5:
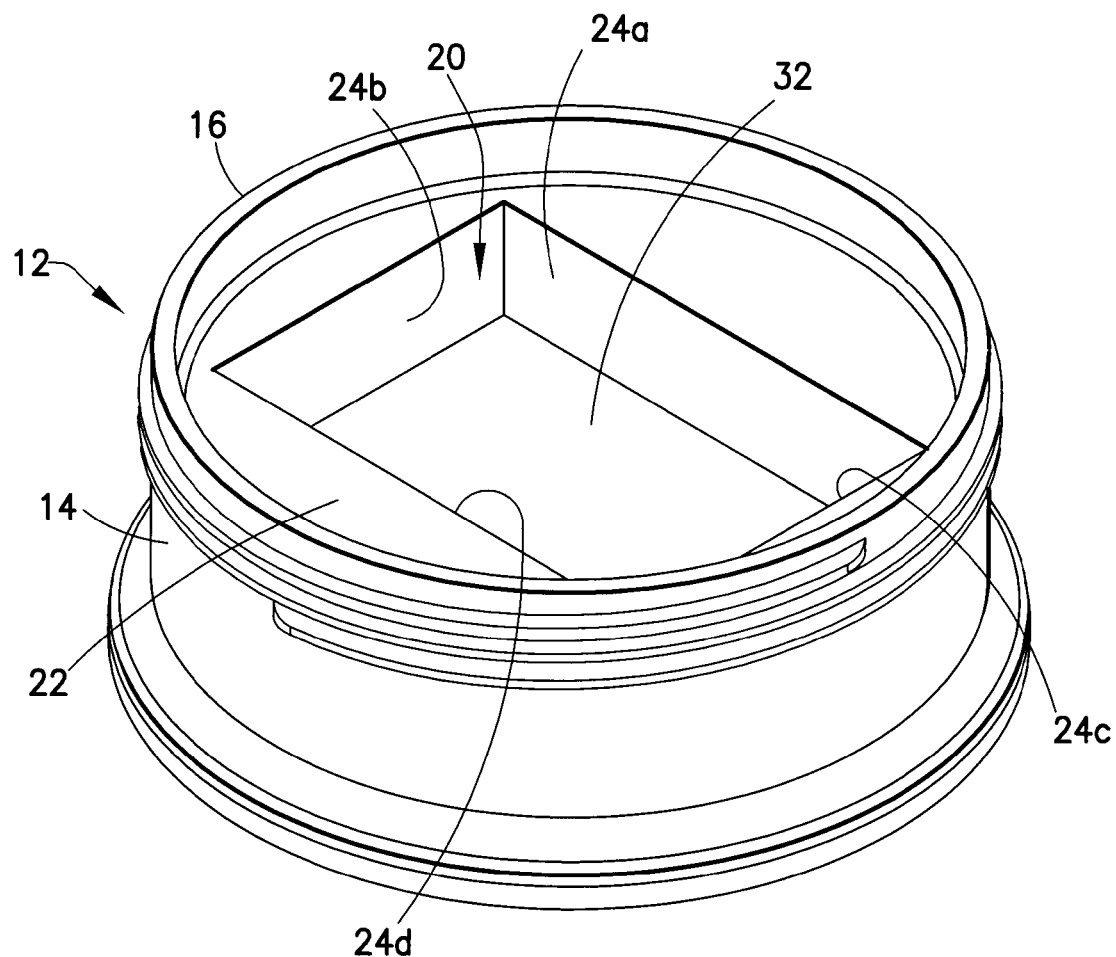
FIG. 5 is a top perspective view of the container housing of the container of FIG. 1 in an embodiment of the present invention.

As noted, sample holder 40 may be provided as a separate element for use within first chamber 20, or may be interconnected with a part of container 10. Desirably, sample holder 40 is mated with closure 50. Such mating may be accomplished by providing sample holder 40 as an integral part connected to or formed with closure 50 or sample holder 40 may be a separate structure that is removably matable or detachably connected with closure 50. As shown in FIG. 4C, closure 50 may include a platform 52 extending from a bottom surface of closure 50 for accommodating sample holder 40 therein. Platform 52 may include structure for maintaining sample holder 40 attached to closure 50 as shown in FIG. 4B, such as in a snap-fit engagement, and sample holder 40 may be releasable from platform 52. In particular, platform 52 may be a generally rectangular structure defining a rectangular recess for accommodating the general size and shape of sample holder 40. Platform 52 may include one or more fingers 62 extending therefrom for engaging with sample holder 40, thereby maintaining sample holder 40 within the recess defined by platform 52. Such fingers 62 may be deflectable, such that when an edge of sample holder 40 adjacent the slanted wall 45 is held in place against a corresponding finger or protrusion 65 of the platform 52 and sample holder 40 is pushed into the recess of platform 52, fingers 62 deflect away from the walls of sample holder 40 and then return to their initial position against nubs 64 of holder 40, thereby snapping sample holder 40 in place. Fingers 62 may lock sample holder 40 in place permanently with respect to platform 52 and closure 50 or may be deflectable so as to remove sample holder 40 from platform 52 if desired.

Platform 52 may also be provided with a general shape so as to permit opening of door 46 of sample holder 40 while maintaining housing 42 of sample holder 40 contained therein, thereby providing access to the interior cavity 44 of sample holder 40 while sample holder 40 is held in place within platform 52 and with respect to closure 50. For example, the wall surface of platform 52 may have a cut-away portion 57 to accommodating a handle-like protrusion 47 of door 46, and the overall dimensions and height of the walls of platform 52 may be designed so as to provide for manually opening of the door 46 by contact of handle 47 and pivoting of door 46 across platform 52 without interference. The walls of platform 52 may further include puncturing elements in the form of piercing points 80, which are oriented in a direction toward breakable membrane 32 and designed to as to pierce or tear through breakable membrane 32 when piercing points 80 are contacted with breakable membrane 32 such as through application of pressure to platform 52 against breakable membrane 32, as will be discussed herein.

Closure 50 may further include a depressible element, such as a depressible button 54, which is downwardly deflectable from the closure 50 into the interior of first chamber 20 of housing 12. Button 54 is interconnected with sample holder 40, such as through platform 52. In particular, button 54 may include a recessed portion 56 on the interior thereof for accommodating an extending finger 58 of platform 52, thereby maintaining platform 52 with respect to button 54 and with respect to closure 50. Button 54 may be constructed of any suitable material adapted to cause the platform to deflect into the interior of first chamber 20, such as a flexible or elastomeric polymer.

As noted above, first chamber 20 may be sized so as to receive and accommodate sample holder 40 therein. In such an arrangement, when sample holder 40 is mated with closure 50 and closure 50 is rotatably engagement with housing 12, such as through a threaded engagement, sample holder 40 may be provided for rotation with respect to closure 50. This may be accomplished, for example, by providing platform 52 as a structure which is rotatable with respect to closure 50, such as through a rotatable connection provided through finger 58 of platform 52 extending within a recessed portion 56 of button 54 of closure 50 and by providing sample holder 40 within platform 52. In this manner, when sample holder 40 is placed within first chamber 20 and closure 50 is rotatably engaged with housing 12, one or both of the platform 52 and/or sample holder 40 will contact one or more of the side wall surfaces 24a, 24b, 24c, and 24d upon rotation of closure 50, thereby maintaining sample holder 40 in place within first chamber 20 of housing 12 of container 10.

Breakable membrane 32 provides housing 12 with structural features, such that first chamber 20 and second chamber 26 may be selectively placed in fluid communication with each other. For example, with breakable membrane 32 extending transversely across the housing 12, first chamber 20 and second chamber 26 are in fluid isolation, such that any fluid contained within the first chamber 20 and/or second chamber 26 is isolated from the other chamber. In order to provide fluid communication between the first chamber 20 and the second chamber 26, the breakable membrane 32 must be broken. Desirably, breakable membrane 32 is constructed of a material that is easily rupturable or broken open by application of pressure thereto. For example, breakable membrane 32 may be a polymeric material, and is desirably a piercable foil, such as those commonly used in the packaging industry.

Container 10 may be assembled and provided with liquid media, such as solutions or reagents, stored within first chamber 20 and/or second chamber 26 at the point of manufacture. Alternatively, any such liquid media may be filled into the first chamber 20 and/or the second chamber 26 at any point prior to use, such as directly prior to inserting a tissue sample into sample holder 40.

As noted, container 10 may be provided for use with a one reagent system. In this manner, a single reagent solution, such as a tissue fixative like formalin, may be provided within second chamber 26. Such fixative solutions stabilize the RNA within a tissue sample for conducting molecular diagnostic testing. Alternatively, container 10 may be provided for use with a two solution or a two reagent system. For example, a wash solution may be provided in second chamber 26, so as to dilute the first reagent fixative in the first chamber 20. It is also possible that each chamber contains the same reagent since it may be advantageous to refresh the same reagent after a period of time has passed. Or, a first reagent solution, such as a tissue fixative like formalin, may be used within first chamber 20, and a second reagent solution, such as a stabilizer in the form of a nucleic acid stabilization reagent, for stabilizing the morphology of the tissue sample, may be provided within second chamber 26.

Any reagents may be used with the container of the present invention. For example, the fixative may be formalin, ethanol solutions, Carnoy's solution I (ethanol and acetic acid), Carnoy's Solution II (ethanol, chloroform and acetic acid), methacarn (methanol, chloroform and acetic acid), Clark's fixative, Boonfix, and the like. A non-limiting list of commercially available fixatives includes, but is not limited to, MIRSKY'S FIXATIVE (available from National Diagnostics, Inc. of Atlanta, Ga.); GLYOFIX (available from Shandon Lipshaw, Inc. of Pittsburgh, Pa.); HISTOCHOICE (available from Amresco); HISTOFIX (available from Trend Scientific, New Brighton, Minn.); KRYOFIX (available from Merck); MICROFIX (available from Energy Beam Sciences, Inc., East Granbury, CT); NEOFIX (available from Merck); NOTOX (available from Earth Safe Industries, Inc., Belle Mead, NJ); OMNIFIX II and OMNIFIX 2000 (available from AnCon Genetics, Inc, Mellville, NY); PREFER (available from Anatech Ltd, Battle Creek, Mich.); PRESERVE (available from Energy Beam Sciences, Inc., East Granbury, CT); SAFEFIX II (available from Thermo Fischer Scientific, Inc.); STATFIX (available from StatLab Medical Products, Inc. of Lewisville, Tex.); STF (Streck Tissue Fixative, available from Streck Laboratories, Omaha, Nebr.); UMFIX (available from Sakura Finetek USA, Inc., Torrance, Calif.); and FINEFIX (available from Milestone Medical of Shelton, Conn.). Commercially available stabilizers include, but are not limited to, RNALATER (available from Ambion, Inc., Austin Tex.; and RNEASY (available from Qiagen, Inc., Valencia, CA). Any other reagents known or hereafter discovered for use as fixatives and/or stabilizers are intended as useful in the present invention.

To assemble container 10, second chamber 26 is filled with the desired liquid medium. In embodiments where second end 18 is a closed end, such liquid medium can be supplied within second chamber 26 through a port or opening. Alternatively, housing 12 is provided with an open second end 18, with cover 28 placed over second end 18 and mated therewith after filling second chamber 26 to contain the liquid medium within second chamber 26. Thereafter, first chamber 20 may be filled with a different liquid medium (for example, in embodiments involving a two reagent system) through first open end 16. Closure 50, with or without sample holder 40 extending therefrom, is then placed over the first open end 16 of housing 12 and threadably mated therewith. The container 10 thus assembled may be packaged in a separate package, if desired, and stored for use.

In use, a biological sample, such as a tissue sample extracted from a patient for molecular or histology diagnostics testing, is placed within cavity 44 within sample holder 40, such as through the hinged door 46. In embodiments where sample holder 40 is provided as a separate element, closure 50 can be removed from housing 12 and sample holder 40 may then be inserted into the platform 52 of closure 50. Alternatively, if sample holder 40 is provided with closure 50, the tissue sample may be placed within sample holder 40 after closure 50 is removed from housing 12, either with sample holder 40 connected thereto or by removing sample holder 40 therefrom and then reattaching it thereto.

Closure 50 with sample holder 40 containing the tissue sample therein is thereafter placed over the first open end 16 of housing 12, with sample holder 40 aligned within and placed into first chamber 20. Closure 50 is then mated with housing 12, such as by rotating closure 50 and/or housing 12 with respect to each other in a threaded engagement. During such respective rotation, sample holder 40 can maintain its orientation within first chamber 20 in embodiments in which first chamber 20 is sized and oriented for accommodating the particular shape of sample holder 40 as discussed above.

In embodiments including a one reagent system as discussed above, the tissue sample at this point is contained within sample holder 40 in first chamber 20 in isolation from the reagent within second chamber 26. When it is desired to contact the tissue sample with the reagent, button 54 is depressed, thereby causing the sample holder 40 connected therewith to move downwardly and contact breakable membrane 32. Such pressure causes breakable membrane 32 to break (as shown in FIG. 6B) to establish fluid communication between first chamber 20 and second chamber 26. Desirably, platform 52 may include a puncture element, such as piercing points 80 on platform 52, that cause breakable membrane 32 to break when button 54 is depressed. In yet a further embodiment, a separate element may be provided extending through a portion of container 10, such as through closure 50 or housing 12, that can be manipulated so as to cause breaking of breakable membrane 32.

After breakable membrane 32 is broken, container 10 may be inverted, shaken, or otherwise moved so as to cause the reagent within second chamber 26 to flow across the barrier point of broken membrane 32 and into first chamber 20, thereby flowing through the fluid openings of sample holder 40 to contact the tissue sample contained within cavity 44 therein. By maintaining the tissue sample separated from the reagent contained within the second chamber 26 in this manner, contact between the sample and the reagent can be precisely regulated until a desired time, and the length of time of contact of the tissue sample and the reagent can be precisely regulated and monitored.

It is further contemplated that a one reagent system can be used wherein the reagent is placed within the first chamber 20 and the tissue sample is immediately contacted with the reagent when placed within the first chamber 20, and after contact for a desired time period, breakable membrane 32 may be broken as noted above, so as to drain the reagent from the first chamber 20 into the second chamber 26, thereby isolating the tissue sample from further contact with the reagent.

In embodiments including a two reagent system as discussed above, when the sample holder 40 is placed within first chamber 20, the tissue sample is placed in contact with the first reagent contained within first chamber 20, with such reagent flowing through the fluid openings 48 of sample holder 40, thereby contacting the tissue sample contained within the internal cavity 44 thereof. The tissue sample can be maintained in contact with the reagent within the first chamber 20 for a specified time period, after which time the breakable membrane 32 may be broken so as to cause fluid flow between the first chamber 20 and the second chamber 26. Thus, the second reagent maintained within second chamber 26 can flow into first chamber 20, thereby contacting the tissue sample contained therein. Moreover, it is contemplated that the first reagent within the first chamber 20 will likewise flow into the second chamber 26, thereby mixing with the second reagent. Accordingly, the concentrations of the first and second reagents can be specifically tailored so as to ensure that any mixing of the two reagents will not have a deleterious effect on the intended functionality of the reagent when contacted with the tissue sample. After the second reagent is displaced into first chamber 20 and contacted with the tissue sample for a desired time period, the closure 50 may be removed so as to remove the tissue sample from sample holder 40 for any desired diagnostic testing.

Since sample holder 40 is connected with closure 50, access to the tissue sample contained within sample holder 40 can be achieved by removing closure 50 from container 10 and inverting it, placing the outer surface on a counter, thereby providing sample holder 40 exposed. Any fluid that is contained within sample holder 40 can drip downward within the bottom or internal surface of closure 50 and be caught by the rim surrounding closure 50, thereby preventing any leakage or spillage onto the counter surface. The hinged door 46 of sample holder 40 may be openable with the sample holder 40 connected with the closure 50, thereby providing a simple access to the tissue sample contained therein and providing a proper support for maintaining the sample holder 40 in place without having to physically contact any portion of the sample holder to hold it in place while accessing the sample, thereby preventing any potential for contamination of the sample based on contact by the user.

Thereafter, the container 10 may be washed and re-used, or more preferably, will be discarded to prevent cross-contamination with other samples.

In a further embodiment shown in FIGS. 7-13B, container 110 includes similar components as the container 10 described above in connection with the embodiment of FIGS. 1-6, but including a rotatable member integrated with the closure as opposed to a depressible member for breaking of the breakable membrane 132. In particular, container 110 includes a housing 112, a first chamber 120, a second chamber 126, at least one, and desirably a pair of breakable membranes 132 and 133, a closure 150 with a sample holder 140, and a rotatable member 160. As with the above described embodiment, the individual components of container 110 may be made of any suitable material that is impervious to liquid and/or gas, such as glass and/or plastic. In one embodiment, the housing 112 may be made of one or more than one of the following representative materials: polypropylene, polyethylene terephthalate (PET), glass, or combinations thereof.

Container 110 generally includes a housing 112 having a housing wall 114 extending between a first open end 116 and a second end 118, defining an axis Y of the container, referred to generally herein as the central or longitudinal axis of the container, along with a container interior. As will be discussed in more detail herein, at least one, and desirably a pair of breakable membranes 132, 133 extends parallel to the axis Y of the container housing 112 separating the container interior into at least a first chamber 120 and a second chamber 126.

In particular, housing wall 114 defines first chamber 120, with first open end 116 extending into the first chamber 120. First chamber 120 defines a first intended fill volume, and may include a cavity that may be sized so as to receive and accommodate sample holder 140 therein. First chamber 120 and second chambers 126 may be established with breakable membranes 132, 133 extend directly between opposing sides of housing wall 114 across the interior of container 112. In one particular embodiment shown in FIG. 8, housing 112 may be configured by arranging a housing insert 113 within the housing interior formed by housing wall 114. Such a housing insert may include a bottom wall surface 122, as well as side wall surfaces 124a and 124b extending from a top plate 125. Breakable membranes 132, 133 extend between bottom wall surface 122 and side wall surfaces 124a, 124b, thereby defining first chamber 120 within the container interior as a generally rectangular-shaped cavity generally corresponding to the size and shape of sample holder 140. In this manner, breakable membranes 132, 133 along with side wall surfaces 124a, 124b and bottom wall surface 122 form first chamber 120 suspended within housing 112, such that second chamber 126 surrounds first chamber 120. Housing 112 may further include support walls 115 extending across opposing portions of housing wall 114 providing support structure for top plate 125 to sit on. Moreover, support walls 115 further define the interior volume of housing 112, thereby providing a desired fill volume for second chamber 126 while maintaining a specified outer diameter for housing 114.

In particular, housing wall 114 further defines second chamber 126 adjacent first chamber 120, separated and isolated therefrom through breakable membranes 132, 133. Second chamber 126 defines a second intended fill volume, which may be different than the first intended fill volume of the first chamber 120. Second chamber 126 may extend to the bottom or second end 118 of housing 112. Second end 118 may be an open end extending into second chamber 126 with container 110 further including a separate cover (not shown) for mating with housing 112 over the second end 118 to provide a closable access to second chamber 126, or second end 118 may be a closed end of container housing 112, with an access port (not shown) provided for filling the interior of second chamber 126.

Sample holder 140 is further provided for use with container 110 and is adapted to be received within first chamber 120 of housing 112. Sample holder 140 is as described above, with like numbers representing like parts. As previously described, sample holder 140 may form a part of container 110 or may be separately provided for use with container 110. Desirably, sample holder 140 includes a closable housing 142 defining an internal cavity 144 for holding a biological tissue sample, with a hinged door-like structure 146, for accessing the internal cavity 144, and with fluid openings 148 adapted to allow fluid to flow therethrough.

Figure 10:
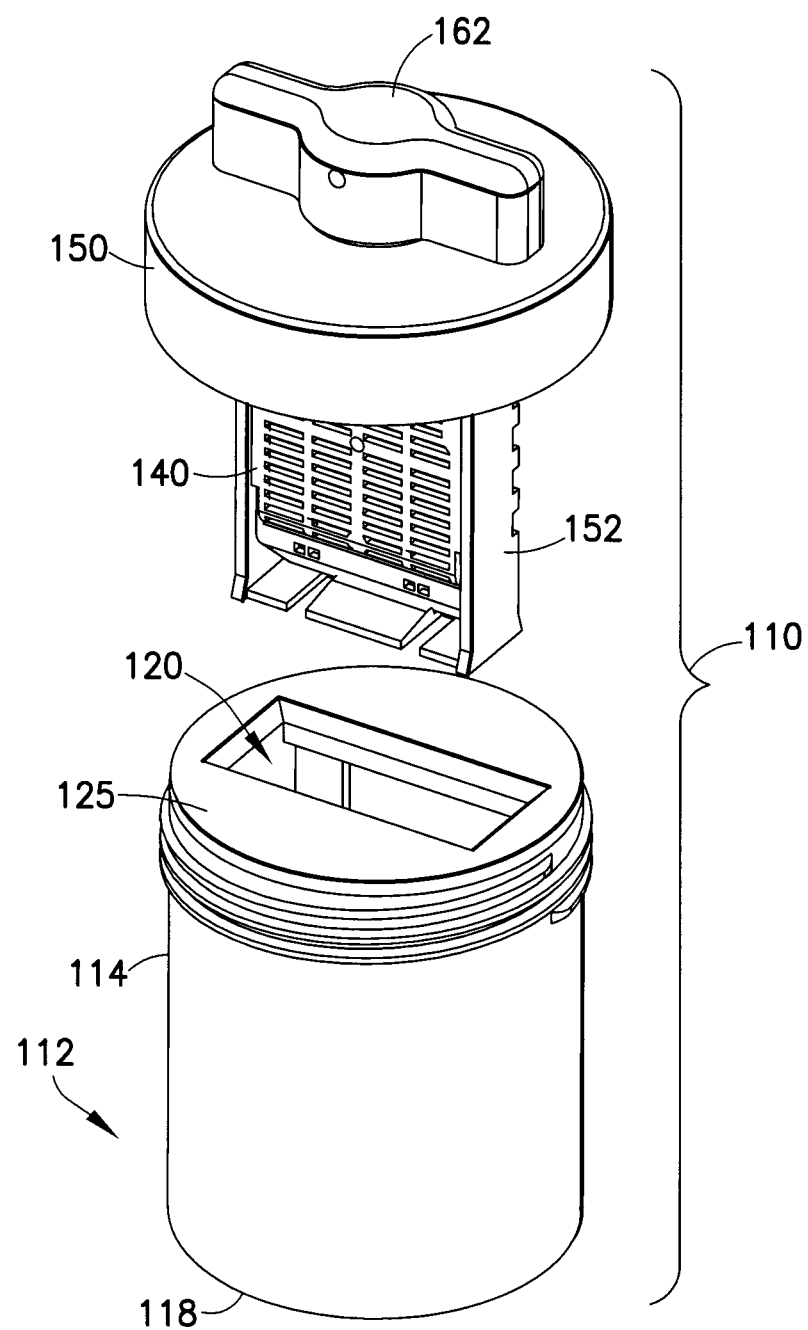
FIG. 10 is a top perspective view of a closure and housing of the container of FIG. 7 in an embodiment of the present invention, including a sample holder.
Figure 11:
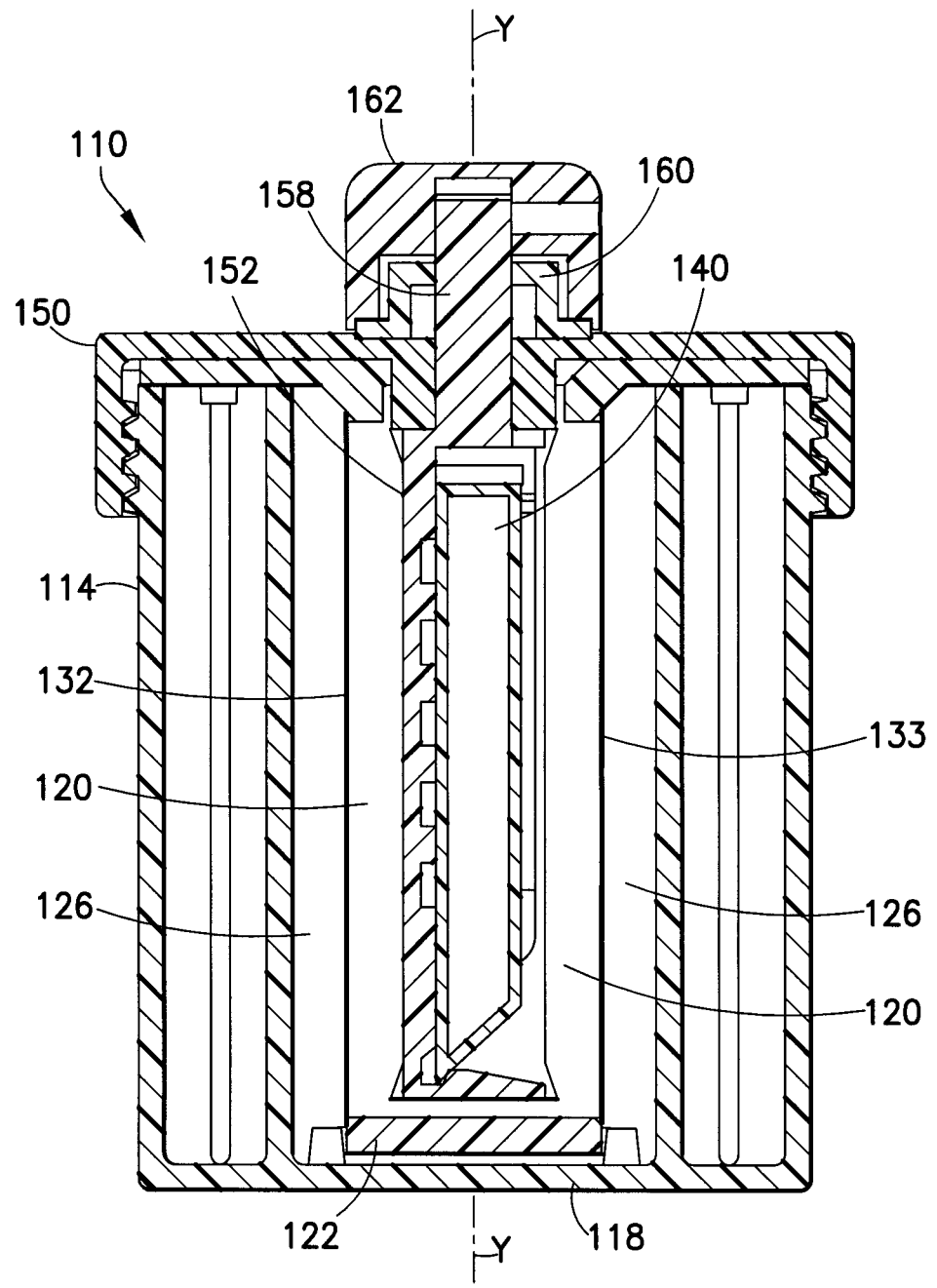
FIG. 11 is a cross sectional view of the container taken along lines 11-11 of FIG. 7.
Figure 12:
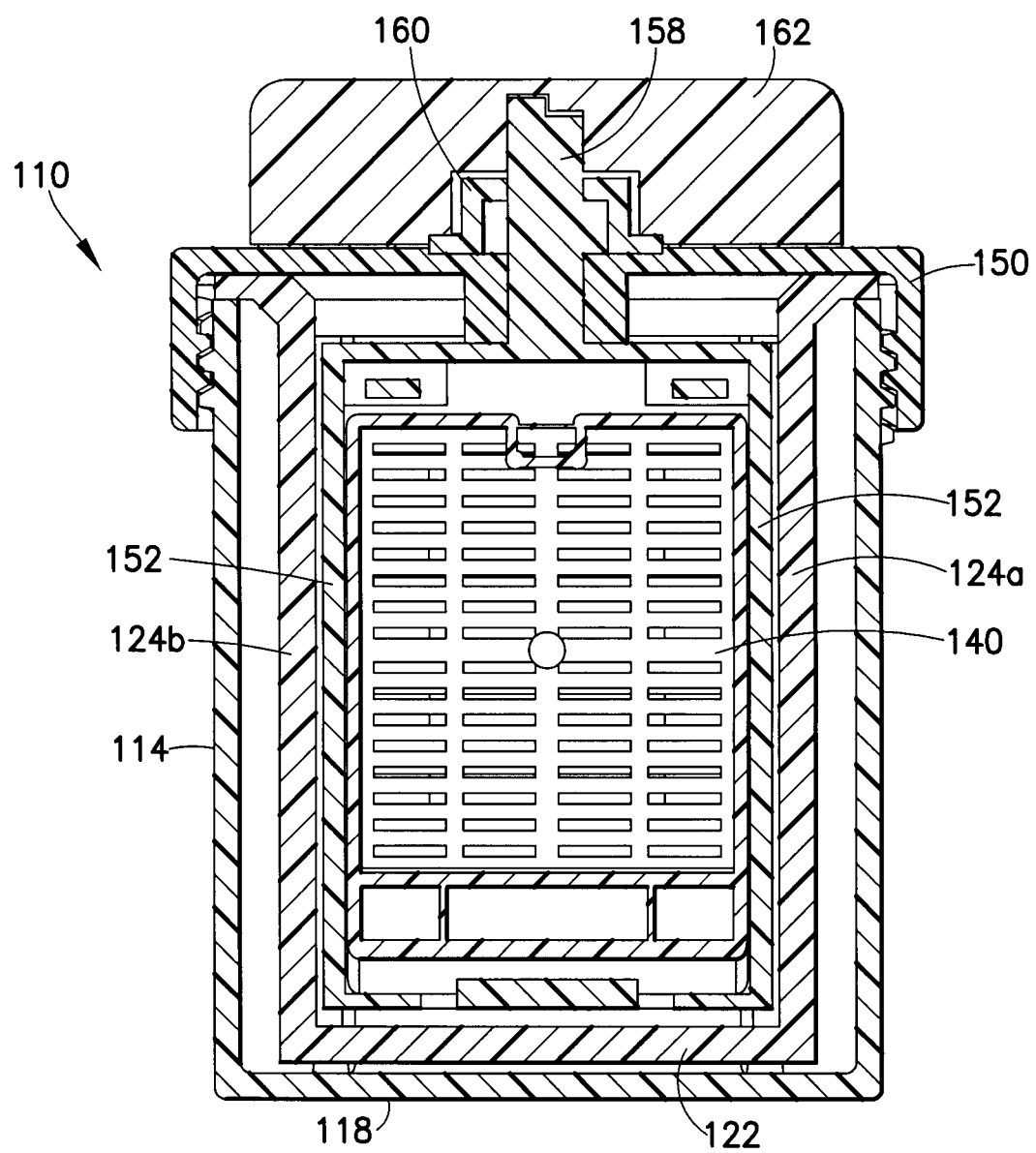
FIG. 12 is a cross sectional view of the container taken along lines 12-12 of FIG. 7.

Container 110 further includes closure 150 for enclosing the first open end 116 of housing 112. Closure 150 is matable with housing 112 at first end 116 in any manner, and desirably, in a threaded engagement with housing 112 to provide a liquid tight seal therebetween as described above. Moreover, sample holder 140 may be mated with closure 150, such as by providing sample holder 140 as an integral part connected to or formed with closure 150 or as a separate structure that is removably matable or detachably connected with closure 150, such as through a platform 152 extending from a bottom surface of closure 150, for accommodating sample holder 140 therein. For example, platform 152 may include structure for maintaining sample holder 140 attached to closure 150 as shown in FIG. 10, such as in a snap-fit engagement, and sample holder 140 may be releasable from platform 152.

As noted above, first chamber 120 may be sized so as to receive and accommodate sample holder 140 therein. In such an arrangement, when sample holder 140 is mated with closure 150 and closure 150 is rotatably engaged with housing 112, such as through a threaded engagement, sample holder 140 may be provided for rotation with respect to closure 150. This may be accomplished, for example, by providing platform 152 as a structure which is rotatable with respect to closure 150, such as through a pivoting connection established between arm 158 of platform 152 extending through closure 150, such as through bushing 160, and connected to an external handle 162, and by providing sample holder 140 within platform 152. In this manner, when sample holder 140 is placed within first chamber 120 and closure 150 is rotatably engaged with housing 112, platform 152 and sample holder 140 will rotate with respect to closure 150, thereby maintaining sample holder 140 in place within first chamber 120 of housing 112 of container 110.

Closure 150 further includes a mechanism for manually causing rotation of platform 152 and sample holder 140 with respect to closure 150. In particular, handle 162 extends through closure 150 and bushing 160, and connects with platform 152 and/or sample holder 140. As such, handle 162 and platform 152 rotate with respect to closure 150. Desirably, the portion of handle 162 that extends externally of container 110 includes finger engaging surfaces and may include structure to define the orientation of sample holder 140 within container 110. Moreover, handle 162 may include a lock so as to prevent rotation of handle 162 with respect to housing 112 until a desired time. Such lock may be in the form of any interference engagement between the platform 152 and a portion of the housing 112 that prevents rotation of the platform 152 to a position that will cause breakable membranes 132, 133 to rupture until a threshold is overcome.

Breakable membranes 132, 133 provide housing 112 with structural features such that first chamber 120 and second chamber 126 may be selectively placed in fluid communication with each other. For example, with breakable membranes 132, 133 extending parallel to the axis defined by the first and second ends of housing 112 between bottom wall surface 122 and side wall surfaces 124a and 124b of housing insert 113, first chamber 120 and second chamber 126 are in fluid isolation, such that any fluid contained within the first chamber 120 and/or second chamber 126 is isolated from the other chamber. In order to provide fluid communication between the first chamber 120 and the second chamber 126, one or both of the breakable membranes 132, 133 must be broken. Desirably, breakable membranes 132, 133 are constructed of a material that is easily rupturable or broken open upon application of pressure thereto, such as a piercable foil, as discussed above. Also, platform 152 may include piercing points 180 for causing such rupturing or tearing of foil upon contact therewith.

Container 110 may be assembled and provided with liquid media, such as solutions or reagents, stored within first chamber 120 and/or second chamber 126, either at the point of manufacture or at any point prior to use. Moreover, container 110 may be provided for use with a one reagent system or a two reagent system, as described in connection with the embodiment of FIGS. 1-6.

To assemble container 110, second chamber 126 is filled with the desired liquid medium, such as through an opening or port, or by providing the second end 118 as an open end with a separate cover. Alternatively, housing 112 may first be filled with the desired liquid medium through first open end 116 and housing insert 113 including breakable membranes 132, 133 contiguous therewith can be inserted into housing 112 through open end 116 and secured in position therein. Thereafter, first chamber 120 may be filled with a different liquid medium (for example, in embodiments involving a two reagent system) through the open end. Closure 150, with or without sample holder 140 extending therefrom, is then placed over the first open end 116 of housing 112 and threadably mated therewith, such as by rotating closure 150 with respect to housing 112. During such rotation, handle 162 rotates with respect to closure 150 through bushing 160, so as to prevent internal rotation of platform 152 and sample holder 140, thereby preventing premature breaking of membranes 132, 133. The container 110 thus assembled may be packaged in a separate package, if desired, and stored for use.

Figure 13A:
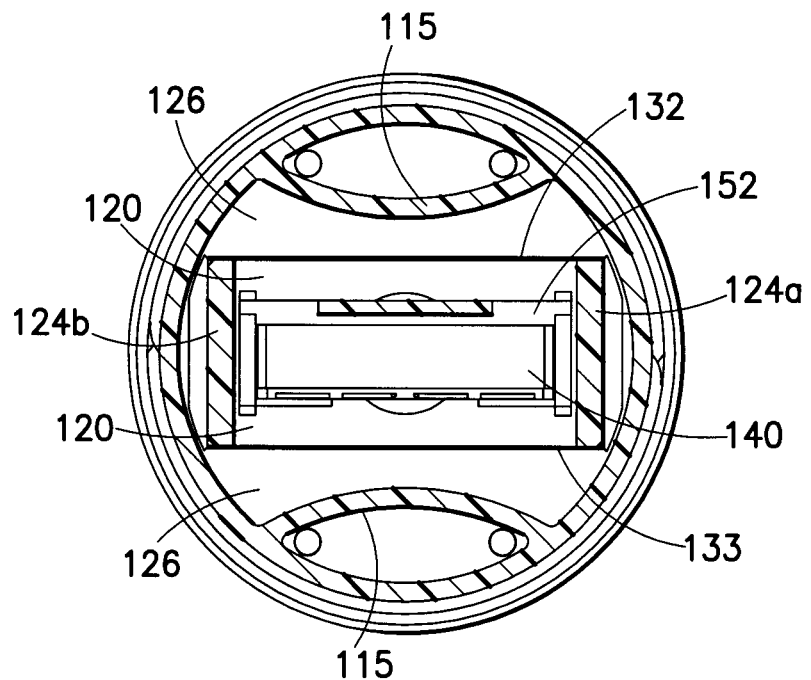
FIG. 13A is a cross sectional view of the container taken along lines 13-13 of FIG. 12 shown with the membrane intact.
Figure 13B:
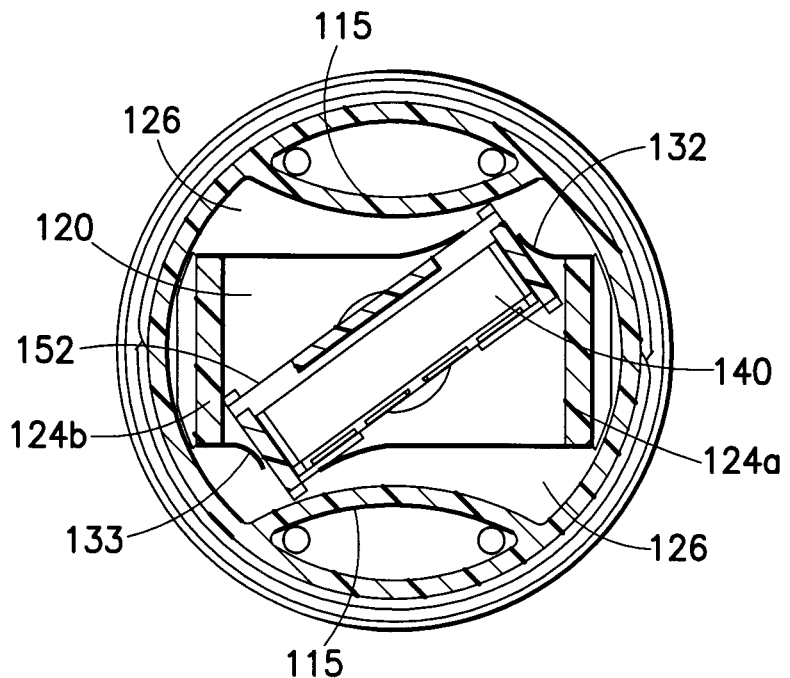
FIG. 13B is a cross sectional view of the container as in FIG. 13A shown with the membrane broken.
Figure 14B:
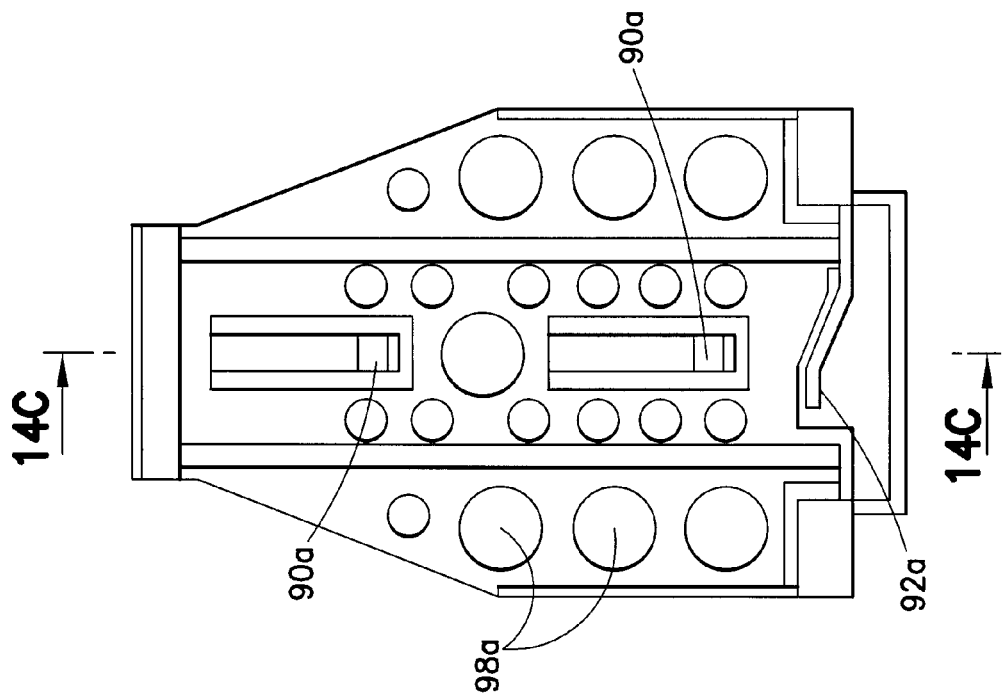
FIG. 14B is a front view of the platform of FIG. 14A.
Figure 14A:
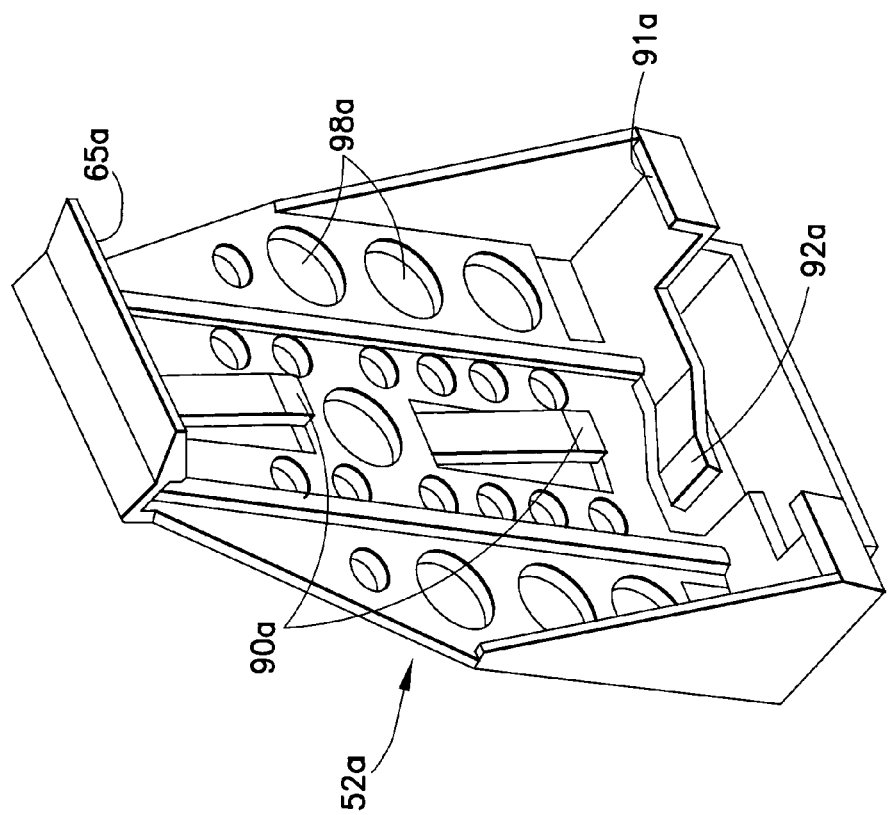
FIG. 14A is a perspective view of an alternative embodiment of a platform for use in connection with the present invention.

In use, a biological sample, such as a tissue sample extracted from a patient for molecular or histology diagnostics testing is placed within cavity 144 within sample holder 140, and closure 150 with sample holder 140 containing the tissue sample therein is thereafter placed over the first open end 116 of housing 112, with sample holder 140 aligned within and placed into first chamber 120, and closure 150 is then mated with housing 112. When it is desired to contact the tissue sample with the reagent in second chamber 126, handle 162 is rotated with respect to container housing 112, thereby causing the sample holder 140 connected therewith through the platform 152 to move about the axis of container 110 and to contact one or both of breakable membranes 132, 133. Such rotation causes piercing points 180 to contact and tear or break through one or both of breakable membranes 132, 133 (as shown in FIG. 13B) to establish fluid communication between first chamber 120 and second chamber 126. Container 110 may be inverted, shaken, or otherwise moved so as to cause the reagent within second chamber 126 to flow across the barrier point of broken membranes 132, 133 and into first chamber 120, thereby contacting the tissue sample contained within sample holder 140 therein.

As noted, container 110 may be used in connection with a one reagent system or a two reagent system as described in connection with the embodiment of FIGS. 1-6. Accordingly, the description of contact of the sample as discussed above applies similarly to the present embodiment.

In one embodiment, the platform may include structure making it capable of accommodating histo-cassettes or sample holders of different sizes and shapes. For example, as shown in an alternate embodiment depicted in FIGS. 14A-14E, platform 52a may include fingers 90a and 92a, which act as compressible elements for bearing against the wall surfaces of sample holders of various sizes. Such fingers 90a and 92a may act as biasing elements or leaf springs for exerting a biasing force against the wall surface of a sample holder placed within platform 52a, biasing the sample holder against the sidewalls of platform 52a to hold the sample holder in place. More particularly, fingers 90a apply a biasing force against a sample holder contained within platform 52a, while opposing surface 91a holds an end of the sample holder therein and finger or protrusion 65a holds a separate edge of the sample holder therein. Also, finger 92a applies a biasing force against the sample holder while opposing protrusion 65a holds the end of the sample holder in place. Such opposite and equal forces assist in maintaining sample holders of various sizes and shapes in place. Further, wall cut-away portion 57a may also be provided for accommodating a handle portion of the door of the sample holder, as discussed above, while also providing access to the handle portion for opening of the door while the sample holder is in place in the platform, if desired. In this manner, container 10 may be provided with a single platform that can accommodate various sizes and shapes of histo-cassettes therein for use with container 10. Additionally, platform 52a may include a plurality of holes 98a for fluid flow therethrough, as discussed above. Such holes 98a may include a pattern or orientation such that fluid flow through the platform to the sample holder will be sufficient for contact with a sample contained within the sample holder regardless of the size, shape, and/or geometry of the sample holder. Such a platform 52a can be used in place of the platforms described above in connection with the embodiments of FIGS. 1-6 or FIGS. 7-13.

While embodiments of the present invention are satisfied in many different forms, there is shown in the figures and described herein in detail specific embodiments of the invention, with the understanding that the present disclosure is to be considered as exemplary of the principles of the invention and is not intended to limit the invention to the embodiments illustrated. Various other embodiments will be apparent to, and readily made by those skilled in the art, without departing from the scope and spirit of the invention. The scope of the invention will be measured by the appended claims and their equivalents.

What is claimed is:

1. A container for storing a biological sample, comprising:
   a housing extending between a first open end and a second end along a central longitudinal axis, the housing defining a container interior having a central longitudinal axis extending from the first open end to the second end along the central longitudinal axis;
   a removable closure for enclosing the first open end; and
   at least one breakable membrane extending within the container interior parallel to the central longitudinal axis and separating the container interior into at least a first chamber and a second chamber in fluid isolation from the first chamber, wherein the first chamber is open to the first open end of the housing and is adapted to receive a sample holder therein, the at least one breakable membrane is breakable to establish fluid communication between the first chamber and the second chamber,
   wherein the first chamber and the second chamber are positioned laterally adjacent to each other perpendicular to the central longitudinal axis.

2. The container of claim 1, wherein the sample holder is detachably connected to the removable closure for insertion into the first chamber of the container interior.

3. The container of claim 1, wherein the removable closure is threadably matable with the housing.

4. The container of claim 1, wherein the sample holder is rotatable with respect to the removable closure to maintain the sample holder in a substantially stationary position within the first chamber during engagement of the removable closure with the housing.

5. The container of claim 1, further comprising a platform attached to the removable closure and adapted for receiving the sample holder for insertion into the first chamber of the container interior.

6. The container of claim 5, wherein the removable closure is threadably matable with the housing and wherein the platform is rotatable with respect to the removable closure to maintain the sample holder in a stationary position within the first chamber during engagement of the removable closure with the housing.

\* \* \* \* \*